(12) United States Patent
Bach et al.

(10) Patent No.: US 11,819,492 B2
(45) Date of Patent: Nov. 21, 2023

(54) NATURAL PRODUCT DERIVATIVES FOR INHIBITING CELLULAR NECROPTOSIS, FERROPTOSIS AND OXYTOSIS

(71) Applicants: Institut National de la Sante et de la Recherche Medicale (INSERM), Paris (FR); Centre National de la Recherche Scientifique (CNRS), Paris (FR); Sorbonne Universite, Paris (FR); Universite de Poitiers, Poitiers (FR); Centre Hospitalier Universitaire de Poitiers, Poitiers (FR)

(72) Inventors: Stéphane Bach, Sibiril (FR); Marie-Thérèse Dimanche-Boitrel, Melesse (FR); Claire Delehouze, La Roche Maurice (FR); Thierry Hauet, Mignaloux Beauvoir (FR)

(73) Assignees: Institut National de la Sante et de la Recherche Medicale (INSERM), Paris (FR); Centre National de la Recherche Scientifique (CNRS), Paris (FR); Sorbonne Universite, Paris (FR); Universite de Poitiers, Poitiers (FR); Centre Hospitalier Universitaire de Poitiers, Poitiers (FR)

( * ) Notice: Subject to any disclaimer, the term of this patent is extended or adjusted under 35 U.S.C. 154(b) by 145 days.

(21) Appl. No.: 17/547,501

(22) Filed: Dec. 10, 2021

(65) Prior Publication Data
US 2022/0096426 A1   Mar. 31, 2022

Related U.S. Application Data

(63) Continuation of application No. 16/342,610, filed as application No. PCT/EP2017/076638 on Oct. 18, 2017, now Pat. No. 11,224,586.

(30) Foreign Application Priority Data

Oct. 18, 2016   (EP) .................................... 16306369

(51) Int. Cl.
*A61K 31/352*   (2006.01)
*A61P 27/02*   (2006.01)
*A61P 25/00*   (2006.01)
*A61K 45/06*   (2006.01)
*C07D 311/20*   (2006.01)
*C07D 311/54*   (2006.01)

(52) U.S. Cl.
CPC ............ *A61K 31/352* (2013.01); *A61K 45/06* (2013.01); *A61P 25/00* (2018.01); *A61P 27/02* (2018.01); *C07D 311/20* (2013.01); *C07D 311/54* (2013.01)

(58) Field of Classification Search
CPC ....... A61K 31/352; A61K 45/06; A61P 27/02; A61P 25/00; C07D 311/20; C07D 311/54
See application file for complete search history.

(56) References Cited

U.S. PATENT DOCUMENTS

| | | |
|---|---|---|
| 2007/0031821 A1 | 2/2007 | Blondel et al. |
| 2011/0092483 A1 | 4/2011 | Blondel et al. |
| 2011/0251428 A1 | 10/2011 | Blondel et al. |
| 2012/0122916 A1 | 5/2012 | Blondel et al. |
| 2019/0262306 A1 | 8/2019 | Bach et al. |

FOREIGN PATENT DOCUMENTS

WO   2013142370 A1   9/2013

OTHER PUBLICATIONS

Hauteville, Marcelle, et al. "Protogenkwanin, a new flavonoid Fromequisetum arvense L." Tetrahedron,. vol. 37, No. 2, Jan. 1, 1981, pp. 377-381, XP055330788, DOI: 10.016/S0040-4020(01)92024-1.

(Continued)

*Primary Examiner* — Jared Barsky
(74) *Attorney, Agent, or Firm* — Banner & Witcoff, Ltd.

(57) ABSTRACT

The present invention relates to a compound of the following general formula (I):

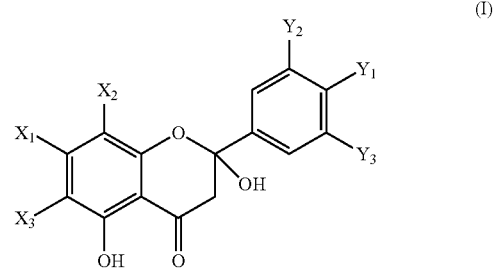

or a pharmaceutically acceptable salt and/or solvate thereof, for use as drug, particularly intended for inhibiting a programmed cell death route selected from the group consisting of ferroptosis, oxytosis and cellular necroptosis. The present invention also relates to a compound of general formula (I) for use as a drug for neuroprotection as well as for preventing and/or treating disorders associated with cellular necroptosis or ferroptosis. The present invention also relates to a pharmaceutical composition comprising a compound of general formula (I), or a pharmaceutically acceptable salt and/or solvate thereof. The present invention also encompasses the use of a compound of the general formula (I) for organs preservation.

11 Claims, 13 Drawing Sheets

(56) References Cited

OTHER PUBLICATIONS

Hauteville, Marcelle, et al. "New type of natural flavonoid. 2,5-dihydroxyflavones. II. Synthesis of some 2,6-hydroxydibenzolymethanes and evidence for their cyclic structure." Bulletin de La Societe Chimique de France, Societe Francaise de Chimie, Paris, France, vol. 5, Jan. 1, 1973, pp. 1784-1788, XP009192890, ISSN: 0037-8968.
Huihui Ti et al. "Stilbenes and flavonoids from *Artocarpus nitidus* subsp. *lingnanensis*". Fitoterapia, vol. 82, No. 4, (2011) 662-665. XP028197897, ISSN: 0367-326X, DOI: 10.1016/j.fitote.2011.02.001.
Miao et al. "Methods to Analyze Cellular Necroptosis", Methods Mol. Biol. 2009, 559, 79-93.
Linkermann et al. "Necroptosis", N. Eng. J. Med. 2014, 370(5), 455-465.
Jouan-Lanhouet et al. "Necroptosis, in vivo detection in experimental disease models" Semin. Cell. Dev. Biol. 2014, 35, 2-13.
Strilic et al. "Tumour-cell-induced endothelial cell necroptosis via death receptor 6 promotes metastasis" Nature 2016, 536(7615), 215-218.
Degterev et al. "Chemical inhibitor of nonapoptotic cell death with therapeutic potential for ischemic brain injury" Nat. Chem. Biol. 2005, 1(2), 112-119.
Degterev et al. "Identification of RIP1 kinase as a specific cellular target of necrostatins" Nat Chem Biol. 2008, 4(5), 313-321.
Cho et al. PLoS One. 2011, 6(8):e23209.
Takahashi et al. "Necrostatin-1 analogues: critical issues on the specificity, activity and in vivo use in experimental disease models" Cell Death Dis. 2012, 3:e437.
Jagtap et al. "Structure-Activity Relationship Study of Tricyclic Necroptosis Inhibitors" J. Med. Chem. 2007, 50(8), 1886-1895.
Teng et al. "Structure activity relationship study of [1,2,3]thiadiazole; necroptosis inhibitors" Bioorg. Med. Chem. Lett. 2007, 17(24), 6836-6840.
Wang et al. "Structure-activity relationship analysis of a novel necroptosis inhibitor, Necrostatin-5" Bioorg. Med. Chem. Lett. 2007, 17(5), 1455-1465.
Zheng et al. "Structure-activity relationship study of a novel necroptosis inhibitor, necrostatin-7" Bioorg. Med. Chem. Lett. 2008, 18(18), 4932-4935.
Wu et al. "A novel necroptosis inhibitor-necrostatin-21 and its SAR study" Bioorg. Med. Chem. Lett. 2013, 23(17), 4903-4906.
Xie et al. "Structural Basis of RIP1 Inhibition by Necrostatins" Structure 2013, 21(3), 493-9.
Yang et al. "Ferroptosis: death by lipid peroxidation" Trends Cell Biol. 2016, 26(3), 165-176.
Chadenson et al. "Synthesis of 2,5-Dihydroxy-7-methoxyflavanoneC, yclic Structure of the Benzoyl-(2 ,6-dihydroxy-4-methoxybenzoyl)-methanfer om Populus nigra Buds" J. Chem. Soc. Chem. Comm. 1972, p. 107-108.
Chadenson et al. Comptes rendus hebdomadaires des séances de l'Académie des sciences. Série C, Sciences chimiques. C. R. Acad. Sc. Paris 1972, 275 p. 1291-1293.
Hanus et al. "Retinal pigment epithelial cell necroptosis in response to sodium iodate" Cell Death Discov. 2016, 2, 16054.
Ahlenstiel et al. "Improved Cold Preservation of Kidney Tubular Cells by Means of Adding Bioflavonoids to Organ Preservation Solutions" Transplantation 2016, 81(2), 231-239.
Cho et al. "RIP1-Dependent and Independent Effects of Necrostatin-1 in Necrosis and T Cell Activation" PLoS One. 2011, 6(8):e2320.
Hauteville, Marcelle et al. (DN 1981:515918 ZCAPLUS, 95:197473a, 19476a, Tetrahedron (1981), 37(2), 377-81, CODEN: TETRAB; ISSN: 0040-4020, Digital Object ID: 10.1016/S0040-4020(01)92024-1, Protogenkwanin, a new flavonoid from Equisetum arvense).

NATURAL PRODUCT DERIVATIVES FOR INHIBITING CELLULAR NECROPTOSIS, FERROPTOSIS AND OXYTOSIS

RELATED APPLICATION DATA

The present application is a continuation application which claims priority to U.S. patent application Ser. No. 16/342,610, filed on Apr. 17, 2019, which is a National Stage Application under 35 U.S.C. 371 of expired PCT application number PCT/EP2017/076638 designating the United States and filed Oct. 18, 2017; which claims the benefit of EP application number 16306369.6 and filed Oct. 18, 2016, each of which are hereby incorporated herein by reference in their entireties.

The present invention relates to a compound for use as a drug, said drug being particularly intended for inhibiting a programmed cell death route selected from the group consisting of ferroptosis, oxytosis and cellular necroptosis. More particularly, the present invention relates to a compound for use for preventing and/or treating disorders associated with cellular necroptosis.

Programmed cell death is a natural process for removing unwanted cells, such as cancer cells.

Necroptosis, a programmed cell death route, is clearly distinct from apoptosis as it does not involve key apoptosis regulators, such as caspases, Bcl-2 family members or cytochrome c release from mitochondria. "Necroptosis" is a specialized biochemical pathway of programmed necrosis that depends notably on the serine/threonine kinase activity of RIPK1 (Receptor-Interacting Protein Kinase 1). It can be inhibited by necrostatin-1, an inhibitor of RIPK1 (U.S. Pat. No. 8,143,300).

Necroptosis may be activated upon stimulation by TNF-α (Tumor Necrosis Factor α), FasL (Fas ligand) and TRAIL (Tumor-necrosis-factor Related Apoptosis Inducing Ligand), and relies on the activity of two serine-threonine kinases, RIPK1 and RIPK3. TNF via TNFR1 (Tumor Necrosis Factor Receptor 1) leads to the formation of two sequential signaling complexes. The receptor-proximal complex I induces pro-survival signals through activation of NF-κB (Nuclear Factor-kappa B) and MAPKs (Mitogen Activated Protein Kinases), while the second cytosolic complex II signals two cell death pathways: (a) apoptosis, via formation of complex IIa including FADD (Fas-Associated Death Domain) that recruits caspase-8 and/or caspase-10 to activate a caspase cascade; (b) necroptosis, via activation of RIPK1 and RIPK3 kinases in a complex called the necrosome. TNF-α can induce necroptosis in Jurkat cells when FADD is deleted (Miao and Degterev, *Methods Mol. Biol.* 2009, 559, 79-93).

The ground-breaking finding that necroptosis is a genetically controlled process led to the hypothesis that this programmed cell-death is druggable, an emerging breakthrough that carries the potential to revolutionize every day clinical medicine (Linkermann and Green, *N. Eng. J. Med.* 2014, 370(5), 455-465). Indeed molecular targets, including RIPK1 (Receptor Interacting Protein 1), RIPK3 and MLKL (Mixed Lineage Kinase domain-Like), have convincingly been shown to contribute to multiple disorders where necroptosis is of central pathophysiological relevance, such as: ischemia-reperfusion injury in brain, heart and kidney, inflammatory diseases, sepsis, retinal disorders, neurodegenerative diseases and infectious disorders (Jouan-Lanhouet et al. *Semin. Cell. Dev. Biol.* 2014, 35, 2-13). More recently, it has been shown that human and murine tumour cells induce necroptosis of endothelial cells, which promotes tumour cell extravasation and metastasis (Strilic et al. *Nature* 2016, 536(7615), 215-218). Necroptosis can thus also be targeted in the treatment of human metastasis, the leading cause of cancer-related death in humans.

Only few RIPK1 inhibitors have been developed (Degterev et al. *Nat. Chem. Biol.* 2005, 1(2), 112-119, and *Nat Chem Biol.* 2008, 4(5), 313-321). Among them, necrostatin-1 (Nec-1) has been used to specifically inhibit several necrotic processes. However, RIPK1-independent effect of Nec-1 has been pointed out (Cho et al. *PLoS One.* 2011, 6(8):e23209), and Nec-1 is also an inhibitor of indoleamine 2, 3-dioxygenase (Takahashi et al. *Cell Death Dis.* 2012, 3:e437). Moreover, the stability of Nec-1 in vivo is very limited. Several structurally distinct necrostatins (Nec-3 (Jagtap et al. *J. Med. Chem.* 2007, 50(8), 1886-1895), Nec-4 (Teng et al. *Bioorg. Med. Chem. Lett.* 2007, 17(24), 6836-6840), Nec-5 (Wang et al. *Bioorg. Med. Chem. Lett.* 2007, 17(5), 1455-1465), Nec-7 (Zheng et al. *Bioorg. Med. Chem. Lett.* 2008, 18(18), 4932-4935)) and corresponding modifications have been reported. Recently, Nec-21, another potent Nec-1 analogue was reported to show an improved off-target profile (Wu et al. *Bioorg. Med. Chem. Lett.* 2013, 23(17), 4903-4906). One of the best stable RIPK1 inhibitor is Nec-1s (Nec-1 stable), which was shown to interact with a hydrophobic pocket of the kinase domain, hence stabilizing RIPK1 in an inactive conformation (Xie et al. *Structure* 2013, 21(3), 493-9).

There is therefore a need for new RIPK1 inhibitors with high potential, good stability and low toxicity.

The inventors of the present invention have thus discovered new inhibitors of the necroptotic cell-death. These compounds thus appear to be very attractive in therapy for preventing and/or treating disorders associated with cellular necroptosis. Moreover, such compounds are also for use for the preservation and/or protection of biological materials such as cells, tissues, body fluids and organs, and of microorganisms, advantageously as a medical device.

Surprisingly, these compounds have proved to be potent inhibitors of two others programmed cell death routes, namely ferroptosis and oxytosis.

Ferroptosis is a non-apoptotic cell death that is catalyzed by iron and is due to a loss of activity of the lipid repair enzyme glutathione peroxidase 4 (GPX4) (Lang and Stockwell, *Trends Cell Biol.* 2016, 26(3), 165-176). The failure of the glutathione-dependent antioxidant defenses leads to an accumulation of lipid-based reactive oxygen species (ROS), resulting notably of lipids peroxidation.

Ferroptosis can be induced by erastin in diverse cell types. The latter is a small molecular inhibitor of the System $X_c$-, a cystine/glutamate antiporter that typically mediates the exchange of extracellular L-cystine and intracellular L-glutamate across the cellular plasma membrane. Once inside a cell, cystine is rapidly reduced to cysteine, which can then enter glutathione (GSH) and protein biosynthetic pathways. This antiporter is thus a key component essential for protection of cells from oxidative stress.

The L-cystine uptake driven by the System $X_c$-is potently inhibited by L-glutamate, inducing an oxidative toxicity. When excessive glutamate is present near nerve cells, a non-apoptotic, oxidative form of cell death occurs, which is called oxytosis. L-glutamate-induced toxicity of neuronal cells is also linked to the excitotoxicity related to the $Ca^{2+}$ uptake. High $Ca^{2+}$ concentrations increase risk for mitochondrial damage. This triggers the mitochondrial production of reactive oxygen species (ROS) that can enhance the effect on the $X_c$-System.

Thus, the present invention relates to a compound of following general formula (I):

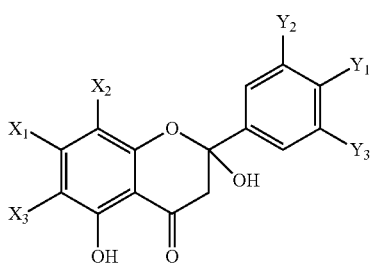

or a pharmaceutically acceptable salt and/or solvate thereof, wherein:
- $X_1$, $X_2$ and $X_3$ each represent, independently of each other, a hydrogen atom; a ($C_1$-$C_6$)alkyl; an aryl; an aryl-($C_1$-$C_6$)alkyl group; an OH; or a group selected from $OR_X$, $SR_X$, $SO_2R_X$ and $NR_XR_Z$,
  with at least one of $X_1$, $X_2$ and $X_3$ representing a ($C_1$-$C_6$) alkyl; an aryl; an aryl-($C_1$-$C_6$)alkyl group; or a group selected from $OR_X$, $SR_X$, $SO_2R_X$ and $NR_XR_Z$, wherein
- $R_X$ is selected from a ($C_1$-$C_6$)alkyl, an aryl and an aryl-($C_1$-$C_6$)alkyl group,
- $R_Z$ is a hydrogen atom or a ($C_1$-$C_6$)alkyl group, and
- the aryl groups are optionally substituted with one or several groups selected from halo, —$OR_1$, —$NR_2R_3$, —$SR_4$, —$S(O)R_5$, —$SO_2R_6$, —$OCOR_7$, —$CO_2R_8$, —$CONR_9R_{10}$, —$CO_2R_{11}$, nitro (—$NO_2$) and cyano (—CN);
- $Y_1$, $Y_2$ and $Y_3$ each represent, independently of each other, a hydrogen atom; a ($C_1$-$C_6$)alkyl; an aryl; an aryl-($C_1$-$C_6$)alkyl group; an OH; or a group selected from $OR_Y$, $SR_Y$, $SO_2R_Y$ and $NR_YR_Z$,
  with at least one of $Y_1$, $Y_2$ and $Y_3$ representing a ($C_1$-$C_6$) alkyl; an aryl; an aryl-($C_1$-$C_6$)alkyl group; or a group selected from $OR_Y$, $SR_Y$, $SO_2R_Y$ and $NR_YR'_Z$, wherein
- $R_Y$ is selected from a ($C_1$-$C_6$)alkyl, an aryl and an aryl-($C_1$-$C_6$)alkyl group,
- $R'_Z$ is a hydrogen atom or a ($C_1$-$C_6$)alkyl group, and
- the aryl groups are optionally substituted with one or several groups selected from halo, —$OR_1$, —$NR_2R_3$, —$SR_4$, —$S(O)R_5$, —$SO_2R_6$, —$OCOR_7$, —$CO_2R_8$, —$CONR_9R_{10}$, —$CO_2R_{11}$, nitro (—$NO_2$) and cyano (—CN);
- $R_1$ to $R_{11}$ are, independently of one another, a hydrogen atom or a ($C_1$-$C_6$)alkyl group, for use as a drug.

In a preferred embodiment:
- $X_1$ represents a ($C_1$-$C_6$)alkyl an aryl, an aryl-($C_1$-$C_6$)alkyl group or an $OR_X$ group, wherein
- $R_X$ is selected from a ($C_1$-$C_6$)alkyl, an aryl and an aryl-($C_1$-$C_6$)alkyl group,
- $X_2$ and $X_3$ each represent, independently of each other, a hydrogen atom or a ($C_1$-$C_6$)alkyl group,
- $Y_1$, $Y_2$ and $Y_3$ each represent, independently of each other, a hydrogen atom, a ($C_1$-$C_6$)alkyl, an aryl, an aryl-($C_1$-$C_6$)alkyl group, an OH or an $OR_Y$ group,
  with at least one of $Y_1$, $Y_2$ and $Y_3$ representing a ($C_1$-$C_6$) alkyl, an aryl, an aryl-($C_1$-$C_6$)alkyl group or an $OR_Y$ group, wherein
- $R_Y$ is selected from a ($C_1$-$C_6$)alkyl, an aryl and an aryl-($C_1$-$C_6$)alkyl group.

For the purpose of the invention, the term "pharmaceutically acceptable" is intended to mean what is useful to the preparation of a pharmaceutical composition, and what is generally safe and non-toxic, for a pharmaceutical use.

The term "pharmaceutically acceptable salt or solvate" is intended to mean, in the framework of the present invention, a salt or solvate of a compound which is pharmaceutically acceptable, as defined above, and which possesses the pharmacological activity of the corresponding compound.

The pharmaceutically acceptable salts comprise:
(1) acid addition salts formed with inorganic acids such as hydrochloric, hydrobromic, sulfuric, nitric and phosphoric acid and the like; or formed with organic acids such as acetic, benzenesulfonic, fumaric, glucoheptonic, gluconic, glutamic, glycolic, hydroxynaphtoic, 2-hydroxyethanesulfonic, lactic, maleic, malic, mandelic, methanesulfonic, muconic, 2-naphtalenesulfonic, propionic, succinic, dibenzoyl-L-tartaric, tartaric, p-toluenesulfonic, trimethylacetic, and trifluoroacetic acid and the like, and
(2) base addition salts formed when an acid proton present in the compound is either replaced by a metal ion, such as an alkali metal ion, an alkaline-earth metal ion, or an aluminium ion; or coordinated with an organic or inorganic base. Acceptable organic bases comprise diethanolamine, ethanolamine, N-methylglucamine, triethanolamine, tromethamine and the like. Acceptable inorganic bases comprise aluminium hydroxide, calcium hydroxide, potassium hydroxide, sodium carbonate and sodium hydroxide.

Acceptable solvates for the therapeutic use of the compounds of the present invention include conventional solvates such as those formed during the last step of the preparation of the compounds of the invention due to the presence of solvents. As an example, mention may be made of solvates due to the presence of water (these solvates are also called hydrates) or ethanol.

The term "stereoisomers" used in this invention refers to configurational stereoisomers, such as optical isomers.

The optical isomers result from the different position in space of substituents comprising four different substituents. This atom thus represents a chiral or asymmetric center. Optical isomers which are not mirror images of one another are thus designated as "diastereoisomers," and optical isomers which are non-superimposable mirror images are designated as "enantiomers".

An equimolar mixture of two enantiomers of a chiral compound is designated as racemate or racemic mixture.

The terms "($C_1$-$C_6$)alkyl", as used in the present invention, refers to a straight or branched saturated hydrocarbon chain containing from 1 to 6 carbon atoms including, but not limited to, methyl, ethyl, n-propyl, iso-propyl, n-butyl, iso-butyl, sec-butyl, t-butyl, n-pentyl, n-hexyl, and the like.

The term "aryl", as used in the present invention, refers to an aromatic hydrocarbon group comprising preferably 6 to 10 carbon atoms and comprising one or more, notably 1 or 2, fused rings, such as, for example, a phenyl or naphtyl group, advantageously a phenyl group.

The term "aryl-($C_1$-$C_6$)alkyl", as used in the present invention, refers to an aryl group as defined above bound to the molecule via a ($C_1$-$C_6$)alkyl group as defined above. In particular, the —($C_1$-$C_6$)alkyl-aryl group is a benzyl group.

The term "halo", as used in the present invention, stands for "halogen", and refers to a fluorine, bromine, chlorine or iodine atom.

According to a particular embodiment of the present invention, $X_1$, $X_2$ and $X_3$ each represent, independently of each other, a hydrogen atom, or a group selected from $OR_X$, $SR_X$, $SO_2R_X$ and $NR_XR_Z$,
with at least one of $X_1$, $X_2$ and $X_3$ representing a group selected from $OR_X$, $SR_X$, $SO_2R_X$ and $NR_XR_Z$.

In another particular embodiment of the present invention,
$X_1$, $X_2$ and $X_3$ each represent, independently of each other, a hydrogen atom; a $(C_1-C_6)$alkyl; an aryl; an aryl-$(C_1-C_6)$alkyl group; an OH; or an $OR_X$ group,
with at least one of $X_1$, $X_2$ and $X_3$ representing an $OR_X$ group.

In still another particular embodiment of the present invention,
$X_1$, $X_2$ and $X_3$ each represent, independently of each other, a hydrogen atom or an $OR_X$ group, with at least one of $X_1$, $X_2$ and $X_3$ representing an $OR_X$ group.

In the above embodiments, $R_X$ is preferably a $(C_1-C_6)$alkyl group, such as methyl, ethyl, n-propyl, more preferably methyl.

In the above embodiments, the aryl groups are optionally substituted with one or several groups selected from halo, $-OR_1$, $-NR_2R_3$, $-SR_4$, $-S(O)R_5$, $-SO_2R_6$, $-OCOR_7$, $-CO_2R_8$, $-CONR_9R_{10}$, $-CO_2R_{11}$, nitro ($-NO_2$) and cyano ($-CN$).

In another embodiment,
$X_1$ represents a $(C_1-C_6)$alkyl; an aryl; an aryl-$(C_1-C_6)$alkyl group; or a group selected from $OR_X$, $SR_X$, $SO_2R_X$ and $NR_XR_Z$, wherein $R_X$ is selected from a $(C_1-C_6)$alkyl, an aryl and an aryl-$(C_1-C_6)$alkyl group, $R_X$ being preferably a $(C_1-C_6)$alkyl group, such as methyl, ethyl, n-propyl, more preferably methyl, and
$X_2$ and $X_3$ each represent, independently of each other, a hydrogen atom or a $(C_1-C_6)$alkyl group, preferably a hydrogen atom.

In still another embodiment,
$X_1$ represents a group selected from $OR_X$, $SR_X$, $SO_2R_X$ and $NR_XR_Z$, wherein $R_X$ is selected from a $(C_1-C_6)$alkyl, an aryl and an aryl-$(C_1-C_6)$alkyl group, $R_X$ being preferably a $(C_1-C_6)$alkyl group, such as methyl, ethyl, n-propyl, more preferably methyl, and
$X_2$ and $X_3$ each represent, independently of each other, a hydrogen atom or a $(C_1-C_6)$alkyl group, preferably a hydrogen atom.

In a preferred embodiment,
$X_1$ represents an $OR_X$ group, $R_X$ being advantageously a $(C_1-C_6)$alkyl group.

In another preferred embodiment,
$X_2$ and $X_3$ each represent a hydrogen atom.

In a yet another preferred embodiment,
$X_1$ represents an $OR_X$ group, wherein $R_X$ is selected from a $(C_1-C_6)$alkyl, an aryl and an aryl-$(C_1-C_6)$alkyl group, $R_X$ being advantageously a $(C_1-C_6)$alkyl group, such as methyl, ethyl, n-propyl, more advantageously methyl, and
$X_2$ and $X_3$ each represent, independently of each other, a hydrogen atom or a $(C_1-C_6)$alkyl group, advantageously a hydrogen atom.

According to a particular embodiment of the present invention,
$Y_1$, $Y_2$ and $Y_3$ each represent, independently of each other, a hydrogen atom, or a group selected from $OR_Y$, $SR_Y$, $SO_2R_Y$ and $NR_YR'_Z$,
with at least one of $Y_1$, $Y_2$ and $X_3$ representing a group selected from $OR_Y$, $SR_Y$, $SO_2R_Y$ and $NR_YR'_Z$.

In another particular embodiment of the present invention,
$Y_1$, $Y_2$ and $Y_3$ each represent, independently of each other, a hydrogen atom; a $(C_1-C_6)$alkyl; an aryl; an aryl-$(C_1-C_6)$alkyl group; an OH; or an $OR_Y$ group, with at least one of $Y_1$, $Y_2$ and $Y_3$ representing an $OR_Y$ group.

In still another particular embodiment of the present invention,
$Y_1$, $Y_2$ and $Y_3$ each represent, independently of each other, a hydrogen atom or an $OR_Y$ group, with at least one of $Y_1$, $Y_2$ and $Y_3$ representing an $OR_Y$ group.

In the above embodiments, $R_Y$ is preferably a $-(C_1-C_6)$alkyl-aryl group, such as benzyl, or naphtylmethyl, more preferably benzyl.

In the above embodiments, the aryl groups are optionally substituted with one or several groups selected from halo, $-OR_1$, $-NR_2R_3$, $-S(O)R_5$, $-SO_2R_6$, $-OCOR_7$, $-CO_2R_8$, $-CONR_9R_{10}$, $-CO_2R_{11}$, nitro ($-NO_2$) and cyano ($-CN$).

In another embodiment,
$Y_1$ represents a $(C_1-C_6)$alkyl; an aryl; an aryl-$(C_1-C_6)$alkyl group; or a group selected from $OR_Y$, $SR_Y$, $SO_2R_Y$ and $NR_YR'_Z$, wherein $R_Y$ is selected from a $(C_1-C_6)$alkyl, an aryl and an aryl-$(C_1-C_6)$alkyl group, $R_Y$ being preferably a $-(C_1-C_6)$alkyl-aryl group, such as benzyl, or naphtyl-methyl, more preferably benzyl, and
$Y_2$ and $Y_3$ each represent, independently of each other, a hydrogen atom or a $(C_1-C_6)$alkyl group, preferably a hydrogen atom.

In still another embodiment,
$Y_1$ represents a group selected from $OR_Y$, $SR_Y$, $SO_2R_Y$ and $NR_YR'_Z$, wherein $R_Y$ is selected from a $(C_1-C_6)$alkyl, an aryl and an aryl-$(C_1-C_6)$alkyl group, $R_Y$ being preferably $-(C_1-C_6)$alkyl-aryl group, such as benzyl, or naphtyl-methyl, more preferably benzyl, and
$Y_2$ and $Y_3$ each represent, independently of each other, a hydrogen atom or a $(C_1-C_6)$alkyl group, preferably a hydrogen atom.

In a preferred embodiment,
$Y_1$ represents an $OR_Y$ group, wherein $R_Y$ is selected from a $(C_1-C_6)$alkyl, an aryl and an aryl-$(C_1-C_6)$alkyl group, $R_Y$ being advantageously a $-(C_1-C_6)$alkyl-aryl group, such as benzyl, or naphtyl-methyl, more advantageously benzyl, and
$Y_2$ and $Y_3$ each represent, independently of each other, a hydrogen atom or a $(C_1-C_6)$alkyl group, advantageously a hydrogen atom.

In the above embodiments, the aryl groups are optionally substituted with one or several groups selected from halo, $-OR_1$, $-NR_2R_3$, $-SR_4$, $-S(O)R_5$, $-SO_2R_6$, $-OCOR_7$, $-CO_2R_8$, $-CONR_9R_{10}$, $-CO_2R_{11}$, nitro ($-NO_2$) and cyano ($-CN$).

According to a first embodiment of the present invention:
$X_1$, $X_2$ and $X_3$ each represent, independently of each other, a hydrogen atom, a $(C_1-C_6)$alkyl an aryl, an aryl-$(C_1-C_6)$alkyl group or an $OR_X$ group,
with at least one of $X_1$, $X_2$ and $X_3$ representing a $(C_1-C_6)$alkyl, an aryl, an aryl-$(C_1-C_6)$alkyl group or an $OR_X$ group, wherein
$R_X$ is selected from a $(C_1-C_6)$alkyl, an aryl and an aryl-$(C_1-C_6)$alkyl group, and
$Y_1$, $Y_2$ and $Y_3$ each represent, independently of each other, a hydrogen atom, a $(C_1-C_6)$alkyl, an aryl, an aryl-$(C_1-C_6)$alkyl group, an OH or an $OR_Y$ group,
with at least one of $Y_1$, $Y_2$ and $Y_3$ representing a $(C_1-C_6)$alkyl, an aryl, an aryl-$(C_1-C_6)$alkyl group or an $OR_Y$ group, wherein $R_Y$ is selected from a ($C_1$-$C_6$)alkyl, an aryl and an aryl-($C_1$-$C_6$)alkyl group.

According to a second embodiment:

$X_1$ represents an $OR_X$ group, wherein $R_X$ is selected from a ($C_1$-$C_6$)alkyl, an aryl and an aryl-($C_1$-$C_6$)alkyl group, $R_X$ being advantageously a ($C_1$-$C_6$)alkyl group, such as methyl, ethyl, n-propyl, more advantageously methyl, $X_2$ and $X_3$ each represent, independently of each other, a hydrogen atom or a ($C_1$-$C_6$)alkyl group, advantageously a hydrogen atom, $Y_1$ represents an $OR_Y$ group, wherein $R_Y$ is selected from a ($C_1$-$C_6$)alkyl, an aryl and an aryl-($C_1$-$C_6$)alkyl group, $R_Y$ being advantageously a —($C_1$-$C_6$)alkyl-aryl group, such as benzyl, or naphtyl-methyl, more advantageously benzyl, and $Y_2$ and $Y_3$ each represent, independently of each other, a hydrogen atom or a ($C_1$-$C_6$)alkyl group, advantageously a hydrogen atom.

According to a third embodiment, the compound for use according to the present invention is of the following formula (II):

(II)

[structure of formula (II)]

or a pharmaceutically acceptable salt and/or solvate thereof, wherein:

$R_X$ represents a ($C_1$-$C_6$)alkyl group, such as methyl, ethyl, n-propyl, more advantageously methyl, and $R_Y$ represents an aryl-($C_1$-$C_6$)alkyl group, such as benzyl, or naphtyl-methyl, more advantageously benzyl.

The compound of general formula (II) can be selected from compounds 1 to 4, represented below, and the pharmaceutically acceptable salts and solvates thereof.

1

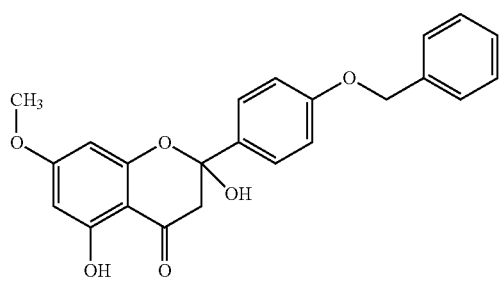

2

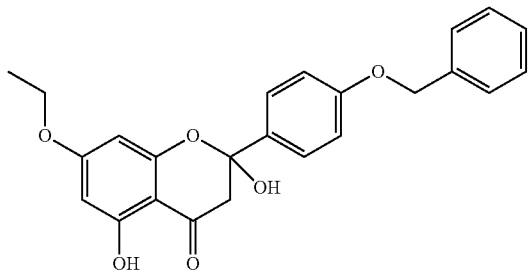

3

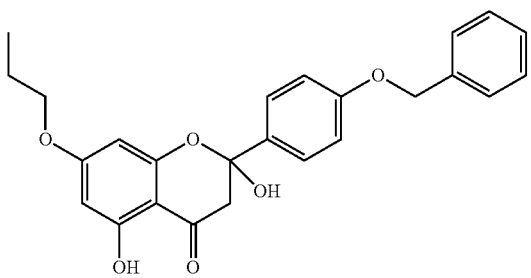

4

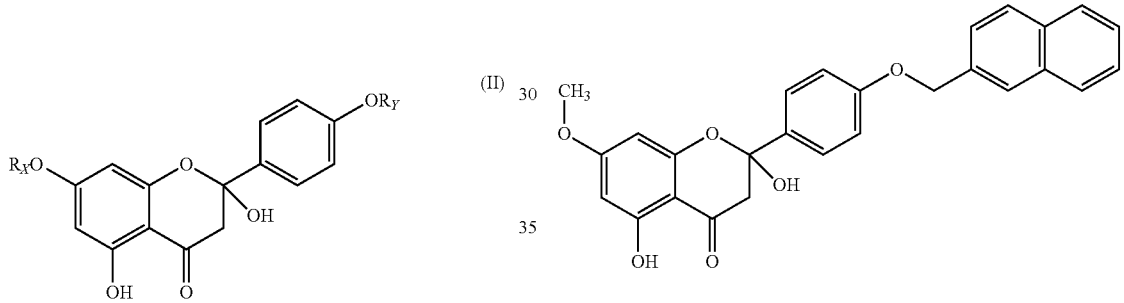

The compound for use according to the present invention is preferably compound 1.

Compound 1 is a synthetic derivative of a naturally occurring flavanone, isolated from *Populus nigra* buds (Chadenson et al. *J. Chem. Soc. Chem. Comm.* 1972, p. 107-108; and Chadenson et al. *C. R. Acad. Sc. Paris* 1972, 275 p. 1291-1293).

The present invention is also directed to the compound of general formula (I) as defined above, for use as a drug intended for inhibiting a programmed cell death route selected from the group consisting of ferroptosis, oxytosis and cellular necroptosis, notably for inhibiting cellular necroptosis.

In particular, the present invention is directed to the compound of general formula (I) as defined above, for use as a drug intended for preventing and/or treating disorders associated with cellular necroptosis.

The cellular necroptosis may be in particular tumour-cell-induced endothelial cell necroptosis.

The disorders associated with cellular necroptosis may be particularly trauma in brain, hepatitis, alcoholic and non-alcoholic steatohepatitis, acute pancreatitis and acute tubular necrosis, heart or kidney transplantation, atherosclerosis, bone marrow failure, viral infection, Crohn's and ulcerative colitis, terminal ileitis, chronic obstructive pulmonary disease or ischemia reperfusion injury such as myocardial infarction or stroke. It can also be age-related macular degeneration, psoriasis or toxic epidermal necrolysis.

The disorders associated with tumour-cell-induced endothelial cell necroptosis may be particularly tumour cells extravasation or metastasis.

In another particular embodiment, the present invention is directed to the compound of general formula (I) as defined above, for use as a drug intended for preventing and/or treating disorders associated with ferroptosis.

The disorders associated with ferroptosis may be particularly acute kidney failure; a neurodegenerative disease such as Huntington's disease, Alzheimer's disease and Parkinson's disease; hemochromatosis; intracerebral hemorrhage (ICH) stroke or ischemia-reperfusion injuries (brain, kidney, hearth).

In still another particular embodiment, the present invention is directed to the compound of general formula (I) as defined above, for use as a drug intended for neuroprotection.

Within the meaning of the present invention, the term "neuroprotection" refers to the relative preservation of neuronal structure and/or function after a deleterious treatment ("a neurodegenerative insult") or in case of pathological conditions. It is thus a treatment option for many central nervous system (CNS) disorders including neurodegenerative diseases such as Parkinson disease, Alzheimer disease, and Amyotrophic Lateral Sclerosis; stroke; traumatic brain injury and spinal cord injury. Despite differences in symptoms or injuries associated with CNS disorders, many of the mechanisms behind neurodegeneration are the same. Common mechanisms include increased levels in oxidative stress and excitotoxicity, which are often targeted by neuroprotective treatments.

The present invention also relates to a method for inhibiting a programmed cell death route selected from the group consisting of ferroptosis, oxytosis and cellular necroptosis, notably for inhibiting cellular necroptosis, comprising the administration to a person in need thereof of an effective dose of a compound of formula (I) as defined above. In particular, the present invention relates to a method for preventing and/or treating disorders associated with cellular necroptosis, comprising the administration to a person in need thereof of an effective dose of a compound of formula (I) as defined above. It also relates to a method for preventing and/or treating disorders associated with ferroptosis, comprising the administration to a person in need thereof of an effective dose of a compound of formula (I) as defined above. It is also directed to a method of neuroprotection, comprising the administration to a person in need thereof of an effective dose of a compound of formula (I) as defined above.

The present invention also relates to the use of a compound of formula (I) as defined above, for the manufacture of a drug, in particular for inhibiting a programmed cell death route selected from the group consisting of ferroptosis, oxytosis and cellular necroptosis, notably for inhibiting cellular necroptosis. In particular, the present invention also relates to the use of a compound of formula (I) as defined above, for the manufacture of a drug for preventing and/or treating disorders associated with cellular necroptosis. It also relates to the use of a compound of formula (I) as defined above, for the manufacture of a drug for preventing and/or treating disorders associated with cellular ferroptosis.

The cellular necroptosis may be in particular tumour-cell-induced endothelial cell necroptosis.

The disorders associated with cellular necroptosis may be particularly trauma in brain, hepatitis, alcoholic and non-alcoholic steatohepatitis, acute pancreatitis and acute tubular necrosis, heart or kidney transplantation, atherosclerosis, bone marrow failure, viral infection, Crohn's and ulcerative colitis, terminal ileitis, chronic obstructive pulmonary disease or ischemia reperfusion injury such as myocardial infarction or stroke. It can also be age-related macular degeneration, psoriasis or toxic epidermal necrolysis.

The disorders associated with tumour-cell-induced endothelial cell necroptosis may be particularly tumour cells extravasation or metastasis.

The disorders associated with ferroptosis may be particularly acute kidney failure; a neurodegenerative disease such as Huntington's disease, Alzheimer's disease and Parkinson's disease; hemochromatosis; intracerebral hemorrhage (ICH) stroke or ischemia-reperfusion injuries (brain, kidney, hearth).

The present invention also relates to the use of a compound of formula (I) as defined above, for the manufacture of a drug intended for neuroprotection.

The present invention also relates to a pharmaceutical composition comprising at least one compound of formula (I) as defined above and at least one pharmaceutically acceptable excipient.

The term "pharmaceutically acceptable excipient" is intended to mean, in the framework of the present invention, a substance which is pharmaceutically acceptable, as defined above, formulated alongside the active ingredient(s) of the pharmaceutical composition, included for the purpose of long-term stabilization, bulking up solid formulations that contain potent active ingredients in small amounts, to confer a therapeutic improvement on the active ingredient in the final dosage form (such as facilitating drug absorption, reducing viscosity, or enhancing solubility), or to enhance the taste or the appearance of the pharmaceutical composition. The appropriate excipients can be easily and wisely selected by the skilled person, taking into account notably the dosage form and the route of administration.

According to one particular embodiment, the present invention is directed to the pharmaceutical composition as defined above, for use for inhibiting a programmed cell death route selected from the group consisting of ferroptosis, oxytosis and cellular necroptosis, notably cellular necroptosis.

According to one particular embodiment, the present invention is directed to the pharmaceutical composition as defined above, for use for preventing and/or treating disorders associated with cellular necroptosis.

According to another particular embodiment, the present invention is also directed to the pharmaceutical composition as defined above, for use for preventing and/or treating disorders associated with ferroptosis.

According to another particular embodiment, the present invention is also directed to the pharmaceutical composition as defined above, for use for neuroprotection.

The present invention also relates to a method for inhibiting a programmed cell death route selected from the group consisting of ferroptosis, oxytosis and cellular necroptosis, notably for inhibiting cellular necroptosis, comprising the administration to a person in need thereof of an effective dose of the pharmaceutical composition as defined above. In particular, the present invention relates to a method for preventing and/or treating disorders associated with cellular necroptosis, comprising the administration to a person in need thereof of an effective dose of the pharmaceutical composition as defined above. It also relates to a method for preventing and/or treating disorders associated with ferroptosis, comprising the administration to a person in need thereof of an effective dose of the pharmaceutical composition as defined above. It is also directed to a method of neuroprotection, comprising the administration to a person in need thereof of an effective dose of the pharmaceutical composition as defined above.

The present invention also relates to the use of the pharmaceutical composition as defined above, for the manufacture of a drug, in particular for inhibiting a programmed cell death route selected from the group consisting of ferroptosis, oxytosis and cellular necroptosis, more particularly for inhibiting cellular necroptosis. In particular, the present invention also relates to the use of the pharmaceutical composition as defined above, for the manufacture of a drug for preventing and/or treating disorders associated with cellular necroptosis. It also relates to the use of the pharmaceutical composition as defined above, for the manufacture of a drug for preventing and/or treating disorders associated with ferroptosis.

The cellular necroptosis may be in particular tumour-cell-induced endothelial cell necroptosis.

The disorders associated with cellular necroptosis may be particularly trauma in brain, hepatitis, alcoholic and non-alcoholic steatohepatitis, acute pancreatitis and acute tubular necrosis, heart or kidney transplantation, atherosclerosis, bone marrow failure, viral infection, Crohn's and ulcerative colitis, terminal ileitis, chronic obstructive pulmonary disease or ischemia reperfusion injury such as myocardial infarction or stroke. It can also be age-related macular degeneration, psoriasis or toxic epidermal necrolysis.

The disorders associated with tumour-cell-induced endothelial cell necroptosis may be particularly tumour cells extravasation or metastasis.

The disorders associated with ferroptosis may be particularly acute kidney failure; a neurodegenerative disease such as Huntington's disease, Alzheimer's disease and Parkinson's disease; hemochromatosis; intracerebral hemorrhage (ICH) stroke or ischemia-reperfusion injuries (brain, kidney, hearth).

The present invention also relates to the use of the pharmaceutical composition as defined above, for the manufacture of a drug intended for neuroprotection.

The pharmaceutical compositions according to the invention may be formulated notably for oral administration or for injection, wherein said compositions are intended for mammals, including humans.

The pharmaceutical composition can be administered orally by means of tablets and gelatin capsules.

When a solid composition is prepared in the form of tablets, the main active ingredient is mixed with a pharmaceutical vehicle such as gelatin, starch, lactose, magnesium stearate, talc, gum arabic and the like. The tablets may be coated with sucrose or with other suitable materials, or they may be treated in such a way that they have a prolonged or delayed activity and they continuously release a predetermined amount of active principle.

A preparation in gelatin capsules is obtained by mixing the active ingredient with a diluent and pouring the mixture obtained into soft or hard gelatin capsules.

For administration by injection, aqueous suspensions, isotonic saline solutions or sterile and injectable solutions which contain pharmacologically compatible dispersing agents and/or wetting agents are used.

The active ingredient may be administered in unit dosage forms of administration, in mixture with standard pharmaceutical carriers, to animals or to humans. The compounds of the invention as active ingredients may be used in doses ranging between 0.01 mg and 1000 mg per day, given in a single dose once per day or administered in several doses throughout the day, for example twice a day in equal doses.

The dose administered per day advantageously is between 5 mg and 500 mg, even more advantageously between 10 mg and 200 mg. It may be necessary to use doses outside these ranges as determined by the person skilled in the art.

The pharmaceutical compositions according to the invention may further comprise at least one other active ingredient, such as another cellular necroptosis inhibitor, or an apoptosis inhibitor, an autophagy inhibitor, a ferroptosis inhibitor, an inhibitor of MPT (The mitochondrial permeability transition) pore-dependent necrosis, a cyclophilin inhibitor, a Cyclin-dependent kinase 5 (CDK5) inhibitor, a parthanatos inhibitor, a thrombin inhibitor, an antioxidant (such as glutathione or allopurinol) or an inflammatory inhibitor.

The present invention relates also to a pharmaceutical composition comprising:
(i) at least one compound of formula (I) or of formula (II) as defined above, and
(ii) at least one other active ingredient, such as another cellular necroptosis inhibitor, or an apoptosis inhibitor, an autophagy inhibitor, a ferroptosis inhibitor, an inhibitor of MPT (The mitochondrial permeability transition) pore-dependent necrosis, a cyclophilin inhibitor, a Cyclin-dependent kinase 5 (CDK5) inhibitor, a parthanatos inhibitor, a thrombin inhibitor, an antioxidant (such as glutathione or allopurinol) or an inflammatory inhibitor,
as a combination product for simultaneous, separate or sequential use.

The present invention also relates to the use of a compound of general formula (I) as defined above; for the preservation and/or protection of biological materials such as cells, tissues, body fluids and organs, and of microorganisms, advantageously as a medical device.

In the context of the present invention, a medical device refers to any product which is put in contact with organs, tissues, cells or products from the human or animal body origin during their conservation, their preparation, their transformation, their packaging or their transport prior to their therapeutic use in humans. A medical device according to the present invention can also be any product coming into contact with embryos in the context of an activity of medically assisted procreation. In particular, this category of products includes graft preservation media (tissues, organs), the media used in the context of in vitro fertilization, or media used during the preparation of cell therapy products.

In particular, the present invention is directed to the use of a compound of general formula (I) as defined above, for use in medium for preserving organs, biological tissue, or living cells, preferably for preserving organs such as for example liver or kidney.

The compound of the invention can thus be used in the case of a graft as a supplementary therapeutic product for preserving cells, tissues or organs between the sampling on a donor and the graft on a receiver.

In another particular embodiment, the present invention also relates to the use of a compound of general formula (I) as defined above as protectant against cold (4° C.) and/or oxidative stress injuries, notably $H_2O_2$-induced necrosis.

In the context of the present invention, "protectant" refers to a substance used to protect biological materials such as cells, tissues, body fluids and organs, and microorganisms from cold damage and/or oxidative stress injuries, notably $H_2O_2$-induced necrosis.

The present invention is also directed to a culture, storage and/or preservation medium comprising at least one compound general formula (I) as defined above.

The examples which follow illustrate the invention without limiting its scope in any way.

Figure 1:
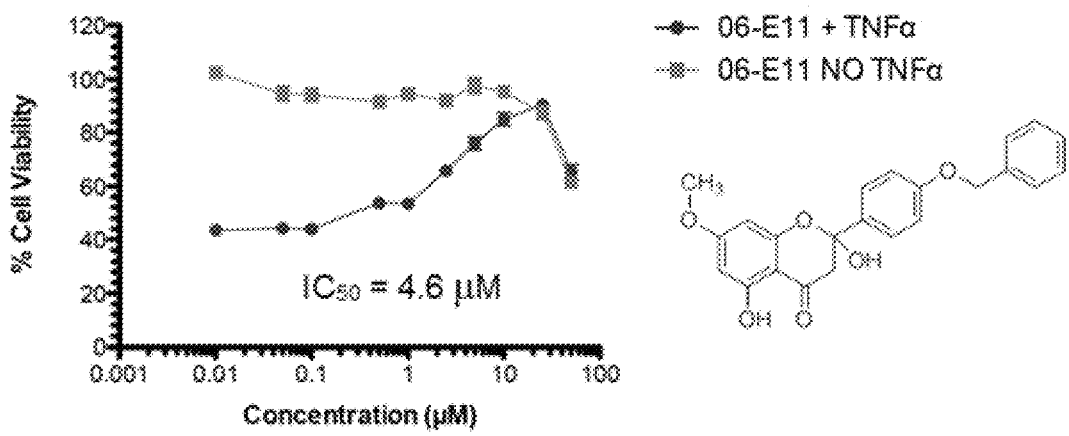
FIG. 1 represents the dose-dependent inhibition by compound 1 of necroptosis induced by TNF-α in human T lymphocyte (Jurkat FADD deficient cell line)

In the above-mentioned figures, "6E11" refers to compound 1.

EXAMPLES

The following abbreviations, commonly used in this field of art, have been used in the following examples:

AGC: Protein kinase A, G, and C families (PKA, PKC, PKG)
BSA: Bovine Serum Albumin
CAMK: Ca$^{2+}$/calmodulin-dependent protein kinases
CMGC: CDKs, MAP kinases, GSK and CDK-like kinases
CDK: Cyclin-dependent kinase
CK1: Cell Kinases 1 (originally known as Casein Kinase 1)
DMF: Dimethylformamide
DMSO: Dimethylsulfoxide
DTT: Dithiothreitol
EC$_{50}$: Half maximal effective concentration
EDTA: Ethylenediaminetetraacetic acid
EGTA: Ethylene glycol-bis(β-aminoethyl ether)-N,N,N,N-tetraacetic acid
Et: Ethyl (CH$_2$CH$_3$)
EtOAc: Ethyl acetate
FACS: Fluorescence-activated cell sorting
FADD: Fas-Associated Death Domain
GSH: glutathione
GSK: Glycogen synthase kinases
GST: Glutathione S-transferase
h: hour
HAEC: Human Artery Endothelial Cells
HB: hydrogen bond
hPBLs: human Peripheral Blood Lymphocytes
hRPE-1: human Retinal Pigment Epithelial cell line
IC$_{50}$: Half maximal inhibitory concentration
Kd: dissociation constant
kg: kilogram
M: Molar
MAP: Mitogen-Activated Protein kinases
MD: Molecular dynamic
Me: Methyl (CH$_3$)
mg: milligram
MHz: MegaHertz
min: minute(s)
ml: milliliter
mM: millimolar
mmol: millimole
MOPS: 3-(N-morpholino)propanesulfonic acid
MTS: 3-[4,5-dimethylthiazol-2-yl]-5-[3-carboxymethoxy-phenyl]-2-[4-sulfophenyl]-2H-tetrazolium
n: number of replicates in an experiment
N: number of independent experiments
NMR: Nuclear Magnetic Resonance
PBS: Phosphate buffered saline
PCR: Polymerase Chain Reaction
RIPK1: Receptor-Interacting Protein Kinase 1
ROS: reactive oxygen species
r.t: Room temperature
SD: Standard Deviation
STE: STE Kinases (Homologs of yeast STErile kinases)
TK: Tyrosine Kinases
TKL: Tyrosine Kinases-Like
TNF-α: Tumor Necrosis Factor α

μg: microgram
μl: Microliter
μM: Micromolar

I. Synthesis of the Compounds According to the Invention

Example 1: Synthesis of the Compounds of General Formula (I)

Compound 1 was prepared according to the method disclosed in Hauteville et al. *Tetrahedron* 1980, 37, p. 377-381.

Said method can be generalized to obtain a compound of general formula (I), according the following reaction scheme:

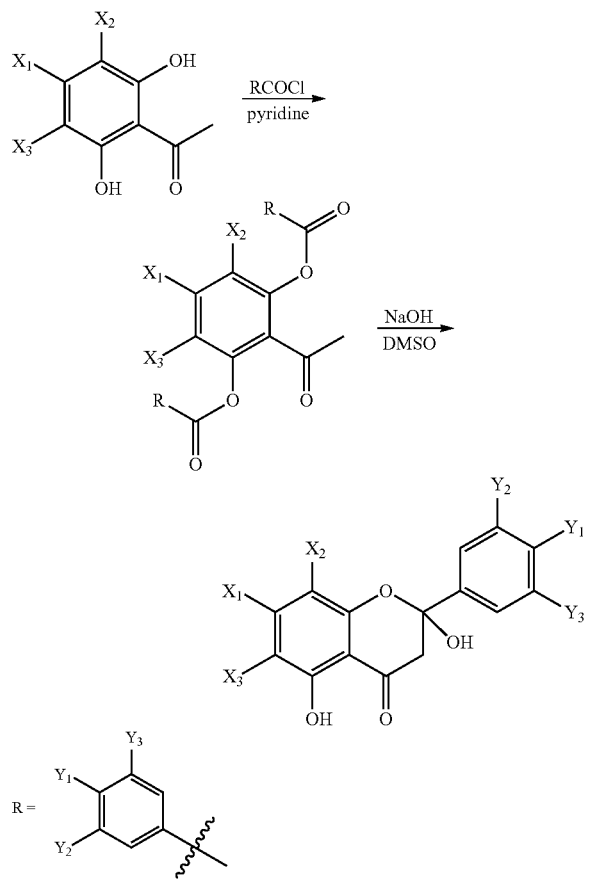

The starting materials are commercially available, or can be easily prepared according to methods well-known of the one skilled in the art. Optionally, and if necessary, additional protection or deprotection steps well-known of the skilled person might be incorporated within the general procedure represented above.

II. Biological Tests of the Compounds According to the Invention

Example 2: Cell-Based Screening of Chemical Libraries for Characterization of Necroptosis Inhibitors TNF-α can induce necroptosis in Jurkat cells (human T lymphocytes) when FADD is deleted. This model was used to screen various libraries of chemical compounds for characterization of new inhibitors of cellular necroptosis. Details on this cell-based assay can be found in Miao and Degterev (*Methods Mol. Biol.* 2009, 559, 79-93). The Jurkat FADD-deficient I 2.1 cell line used was purchased from ATCC and was maintained in RPMI 1640 medium (Gibco) containing Glutamax and 15% fetal calf serum (Life Technology). Necroptosis was induced by addition of 10 ng/ml of human recombinant TNF-α (Life Technology). Necrostatin-1 (Nec-1, Enzo Life Sciences) was used as model necroptosis inhibitor. Cells were maintained in 75 cm$^2$ flask and passed every 2 or 3 days. Chemical collections analysed were formatted in 96-well plates with 80 molecules per plate at 10 mM in 100% DMSO. For each collection plate, two plates were prepared: one corresponding to necroptosis-induced with TNF-α, and the other without TNF-α to evaluate the intrinsic toxicity of the tested compound. Cells were seeded at 20000 cells/well, in 40 μl of medium, in a 96-well clear, flat bottom plate (CytoOne, Starlab) before treatment. Then, 40 μl of medium with or without TNF-α at 25 ng/ml were added to all wells in the corresponding plate. Immediately after TNF-α addition, 20 μl of diluted compound at 50 μM were added to the plates. Final concentration of each chemical compound was 10 μM at 0.1% DMSO. Eight positives (Nec-1 at 10 μM final) and eight negative (DMSO) controls were used in each plate to validate the assay. Cells were incubated at 37° C., 5% CO$_2$ for 24 hours before performing MTS viability assay, described hereafter. Compounds were diluted before to treat cells. Liquid handling was performed using the Nimbus Microlab liquid handler (Hamilton Robotics) under microbiological safety workbench. The 10 mM compounds were diluted at 50 μM directly in cell medium.

Compound 1 has emerged from this screening to be a very efficient necroptosis inhibitor, as discussed below.

Example 3: Anti-Necrotic Effect of Compound 1

Effect on cell viability: Jurkat FADD-deficient I 2.1 cells were treated by TNF-α (10 ng/ml) and increasing concentrations of compound 1 (0.01-0.05-0.10-0.50-1.00-2.50-5.00-10.00-25.00-50.00 μM). Cells were incubated at 37° C., 5% CO$_2$ for 24 hours before performing MTS viability assay. Cell viability was monitored using CellTiter 96® AQueous Non-Radioactive Cell Proliferation Assay (Promega, Fitchburg, WI, USA), based on the water-soluble tetrazolium compound MTS (3-[4,5-dimethylthiazol-2-yl]-5-[3-carboxymethoxy-phenyl]-2-[4-sulfophenyl]-2H-tetrazolium, inner salt) according to the manufacturers instructions. As it appears from FIG. 1, compound 1 protects cells from death induced by TNF-α.

Figure 2:
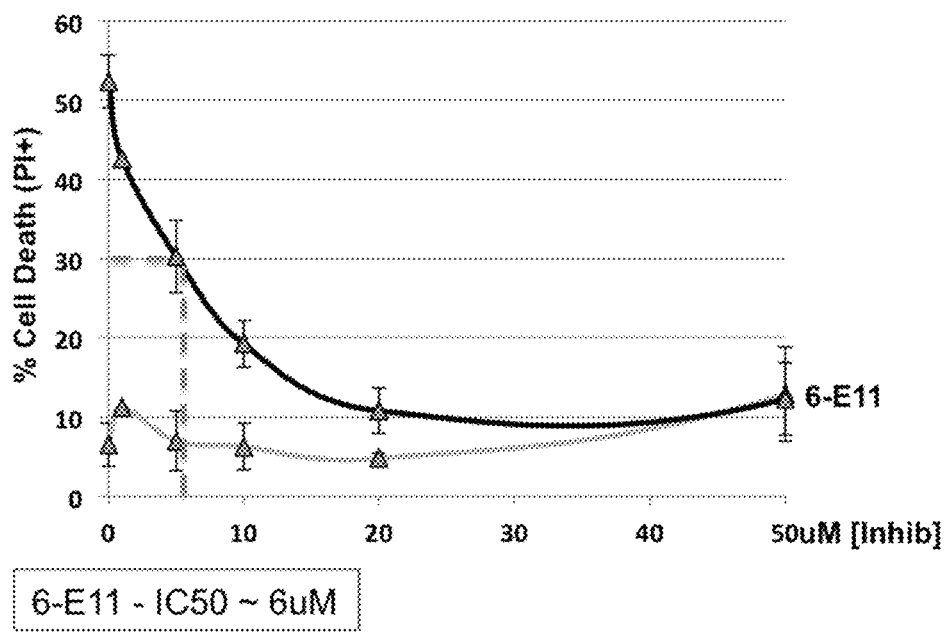
FIG. 2 represents the dose-dependent inhibition by compound 1 of the cell membrane permeabilization induced by TNF-α in human T lymphocyte (Jurkat FADD deficient cell line) (the light grey curve is obtained when cells are treated with compound 1 only)
Figure 3:
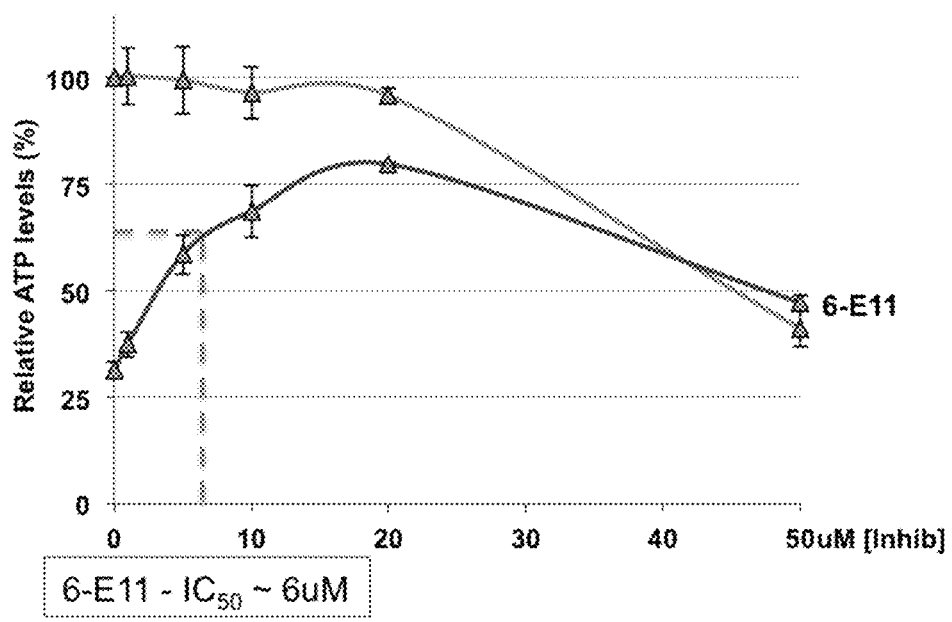
FIG. 3 represents the dose-dependent inhibition by compound 1 of the ATP depletion induced by TNF-α in human T lymphocyte (Jurkat FADD deficient cell line) (the light grey curve is obtained when cells are treated with compound 1 only)

Effect on two hallmarks of necroptosis: Jurkat FADD-deficient I 2.1 cells were treated by TNF-α (10 ng/ml) and increasing concentrations of compound 1 (0, 1, 5, 10, 20 and 50 μM). Cells untreated by TNF-α are used as control (light grey curves). Cells were incubated at 37° C., 5% CO$_2$ for 24 hours before performing the measurements of both plasma membrane permeabilization and intracellular ATP levels. Dead cells were detected by FACS analysis of Propidium Iodide-stained nuclei (FIG. 2). ATP Quantification is performed using the CellTiter-Glo® Luminescent Cell Viability Assay. The luminescent signal produced by a luciferase reaction is proportional to the amount of ATP present and the amount of ATP is directly proportional to the number of metabolically active cells (n=4) (FIG. 3). As reported on FIGS. 2 and 3, compound 1 inhibits two major hallmarks on necroptosis induced by TNF-α.

Example 4: Compound 1 Cytotoxicity Assays

On Human Peripheral Blood Lymphocytes (hPBLs):

hPBLs were treated with increasing concentrations of compound 1 (0, 1, 5, 10, 20, 50 and 100 µM) for 24 hours. Viability was assessed by cell proliferation assay (MTS). % of cell viability was determined using the CellTiter 96® AQ$_{ueous}$ Non-Radioactive Cell Proliferation Assay (Promega). Data represent the quantitative analysis of six independent experiments with means±SD (n=6 individuals).

Figure 4:
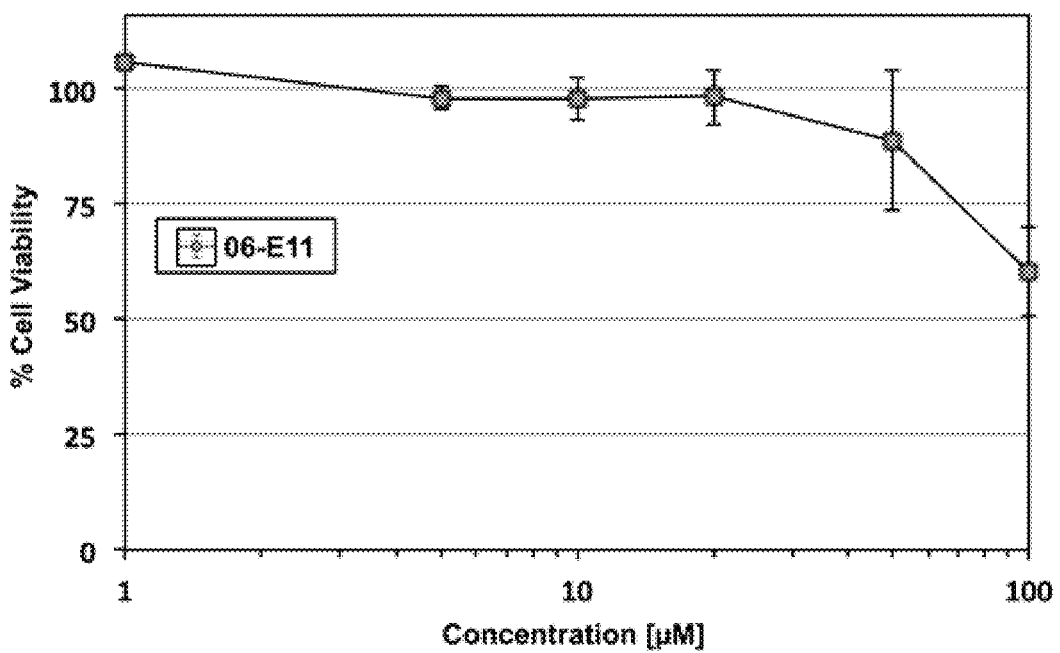
FIG. 4 represents the viability of human primary blood leukocytes treated with increasing concentrations of compound 1.

As it appears from FIG. 4, compound 1 is not cytotoxic towards hPBLs up to a concentration of 20 µM.

On the Human Retinal Pigment Epithelial Cell Line (hRPE-1):

hRPE-1 cells were treated with increasing concentrations of compound 1 (0, 0.01, 0.05, 0.1, 0.5, 1, 2.5, 5, 10, 25 and 50 µM) for 24 hours. A colorimetric MTS assay was used to calculate the percentage of cell viability.

Figure 5:
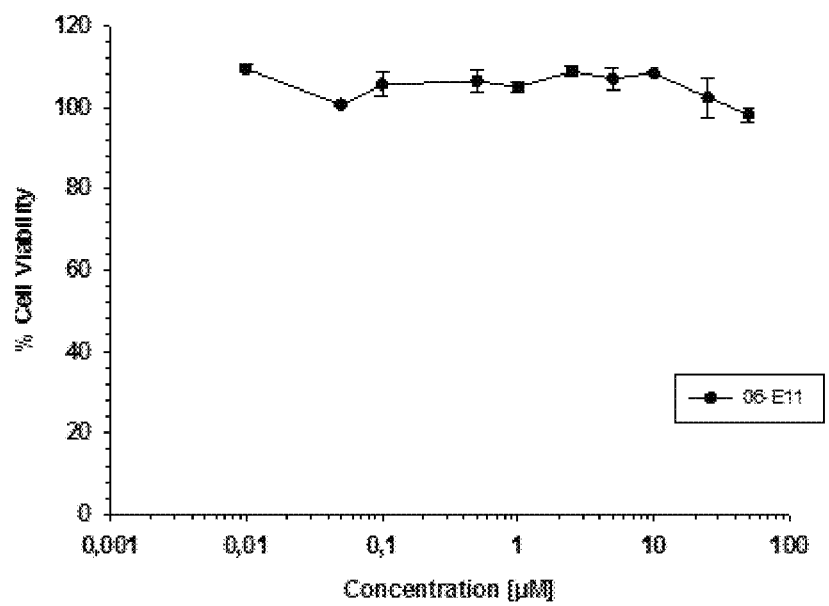
FIG. 5 represents the viability of human retinal pigment epithelial cells treated with increasing concentrations of compound 1.

As it appears from FIG. 5, compound 1 is not cytotoxic towards hRPE-1 cells at the tested concentrations.

Example 5: RIPK1 Autophosphorylation Assay and Binding Assays

RIPK1 Autophosphorylation Assay:

Human RIPK1 full length GST-tagged was baculovirally expressed in Sf9 cells according to manufacturer's instructions (Bac-to-Bac expression system, Invitrogen) and purified using gluthation-sepharose beads (GE Healthcare). The elution was made in 50 mM Tris-HCl, pH 8.0 buffer supplemented with 30 mM reduced gluthathione (Sigma). The protocol used to detect the enzymatic activity is adapted from Miao and Degterev (*Methods Mol. Biol.* 2009, 559, 79-93). Kinase reaction was initiated mixing 5 µl of eluted RIPK1, 5 µl of 3X kinase reaction buffer (5 mM MOPS pH 7.2, 2.5 mM β-glycerophosphate, 4 mM MgCl$_2$, 2.5 mM MnCl$_2$, 1 mM EGTA, 0.4 mM EDTA, 50 µg/ml BSA, 0.05 mM DTT), 2 µl H$_2$O and 3 µl of the tested molecule. The mixture was kept on ice for 10 minutes. During the incubation, the ATP solution was prepared by mixing 5 µl of 3X kinase reaction buffer, 4 µl H$_2$O, 6 µl cold ATP at 150 µM and 2 µCi of [γ-$^{32}$P] ATP. The ATP solution and the tested inhibitor were added to the kinase and incubated for 30 minutes at 30° C. To stop the enzymatic reaction, 5 µl of loading buffer were added and solution was heated for 3 minutes at 95° C. 25 µl of each reaction were loaded per well in pre-cast NuPage 12% Bis-Tris gel (Life Technology). Necrostatin-1, a well-described inhibitor of RIPK1, was used as an internal control. Coomassie staining was performed in order to estimate the total amount of protein loaded on polyacrylamide gel. Autophosphorylated RIPK1 band was visualized on radiographic film after 6h exposition at −80° C.

Figure 6:
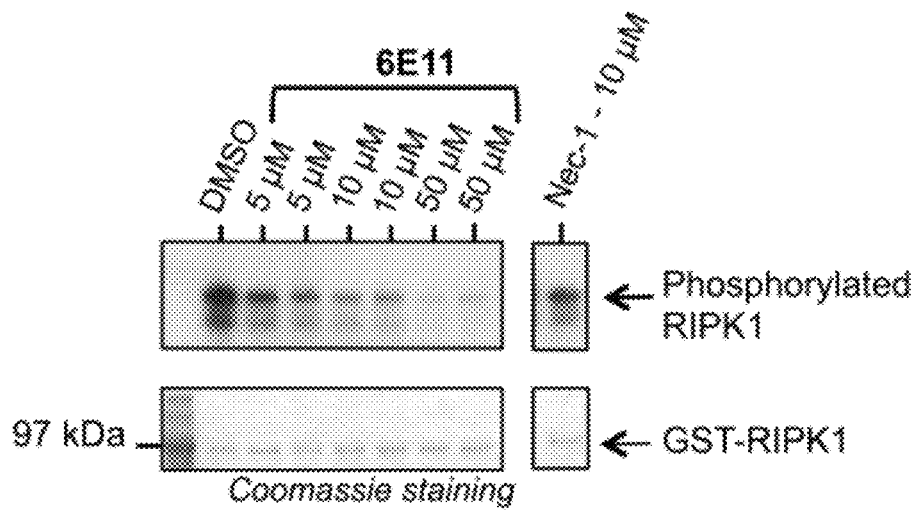
FIG. 6 represents the dose-dependent inhibition of RIPK1 autophosphorylation by compound 1.

The results of this test obtained with compound 1 are indicated in FIG. 6. The decrease of the amount of radioactively labeled RIPK1 indicates that compound 1 inhibits the RIPK1 autophosphorylation in a dose-dependent way.

Figure 7:
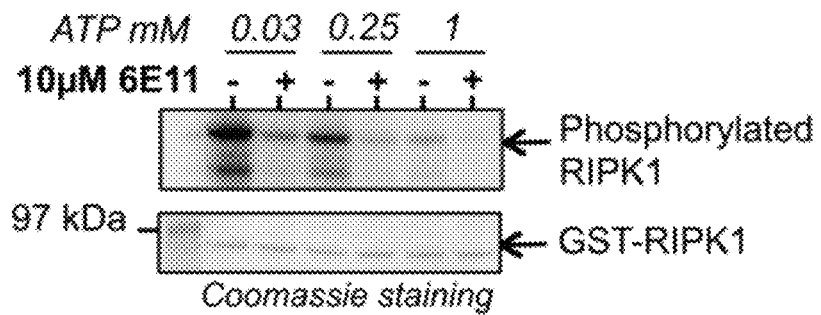
FIG. 7 represents the inhibition of RIPK1 autophosphorylation by compound 1 at high ATP concentrations (up to 1 mM)

Besides, as shown in FIG. 7, the inhibition of RIPK1 auto-phosphorylation by compound 1 is not affected by high ATP concentrations (e.g. 1 mM), which suggests that compound 1 is a non-ATP competitive inhibitor.

Binding Assays:

(i) Characterization of Kinase Targets of Compound 1 ("KINOMEscan Max").

Figure 8:
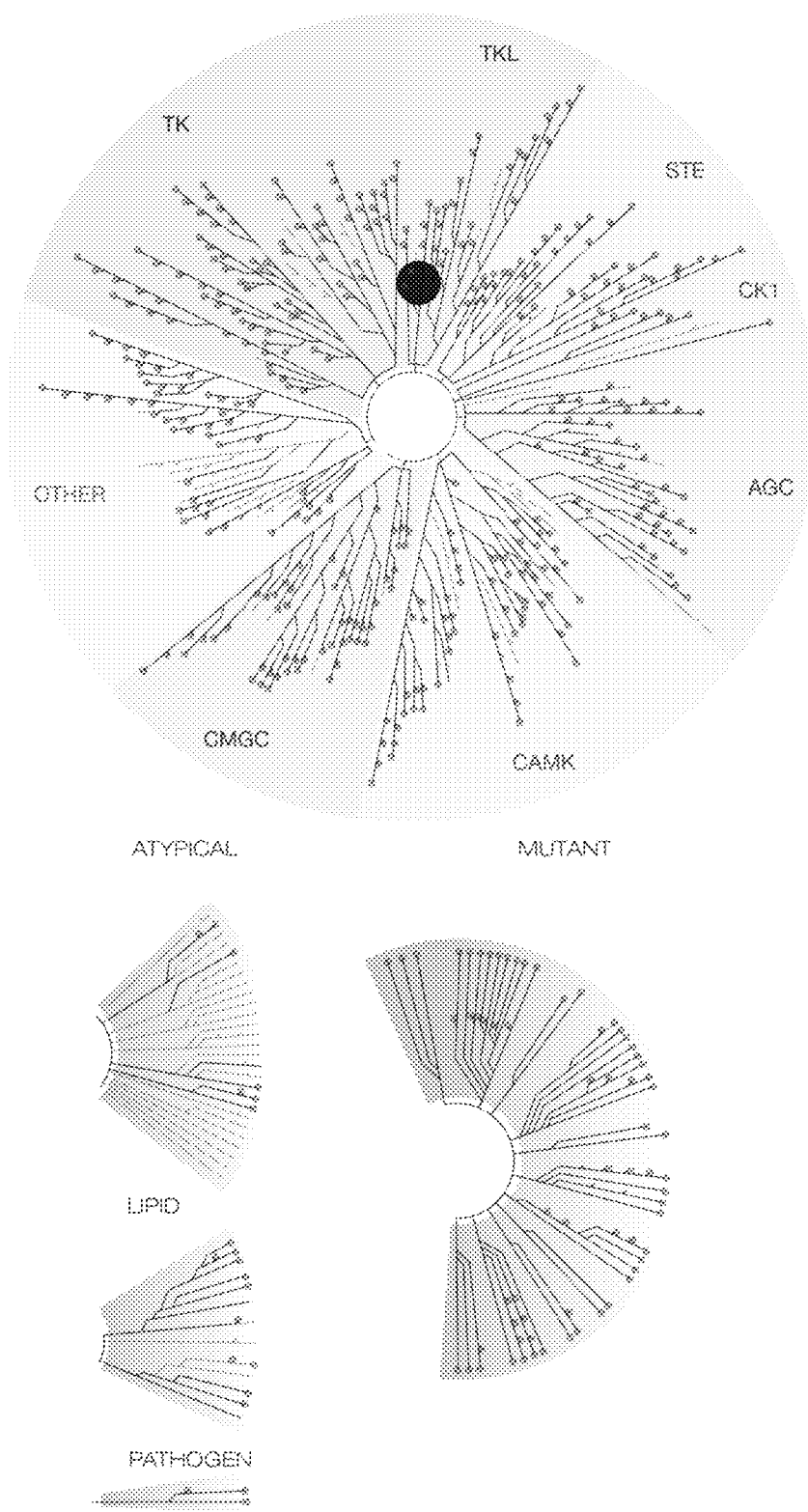
FIG. 8 represents the analysis of compound 1 selectivity against a large panel of kinases.

This in vitro competition binding assay was used for the profiling of compound 1 against 456 kinases, including eight lipid kinases. This experimental approach quantitatively measures the ability of a compound to compete with an immobilized, active-site directed ligand. The assay is performed by combining three components: DNA-tagged kinase (e.g. RIPK1); immobilized ligand; and a test compound (here compound 1). The ability of compound 1 to compete with the immobilized ligand is measured via quantitative PCR of the DNA tag. The codes reported on the FIG. 8 indicate the subclasses of protein kinases: CMGC for CDKs, MAP kinases, GSK and CDK-like kinases; AGC for Protein kinase A, G, and C families (PKA, PKC, PKG); CAMK for Ca2+/calmodulin-dependent protein kinases; CK1, Cell Kinases 1 (originally known as Casein Kinase 1); STE, STE Kinases (Homologs of yeast STErile kinases); TKL, Tyrosine Kinases-Like; TK, Tyrosine Kinases. Each kinase tested in the assay panel is marked with a circle. The hit kinase reported, RIPK1, is marked with a black circle. The size of the circle is proportional to the binding efficiency of compound 1 to the kinase of interest. Small grey dots represent only poor affinity for the tested kinase (as over 30% of the tested kinase are still on the affinity matrix after competition with the tested compound, here compound 1). For RIPK1, only 0.15% of the initial amount of kinase is still on the affinity matrix after competition with compound 1. The graphic representation of the human kinome phylogenetic tree (TREEspot™ Kinase dendrogram,© DiscoveRx, Fremont, USA), reported on FIG. 8, illustrates the high specificity of compound 1 for RIPK1 among the large panel of tested kinases.

(ii) Determination of Dissociation Constant (Kd) of Compound 1 for RIPK1 Kinase.

Figure 9:
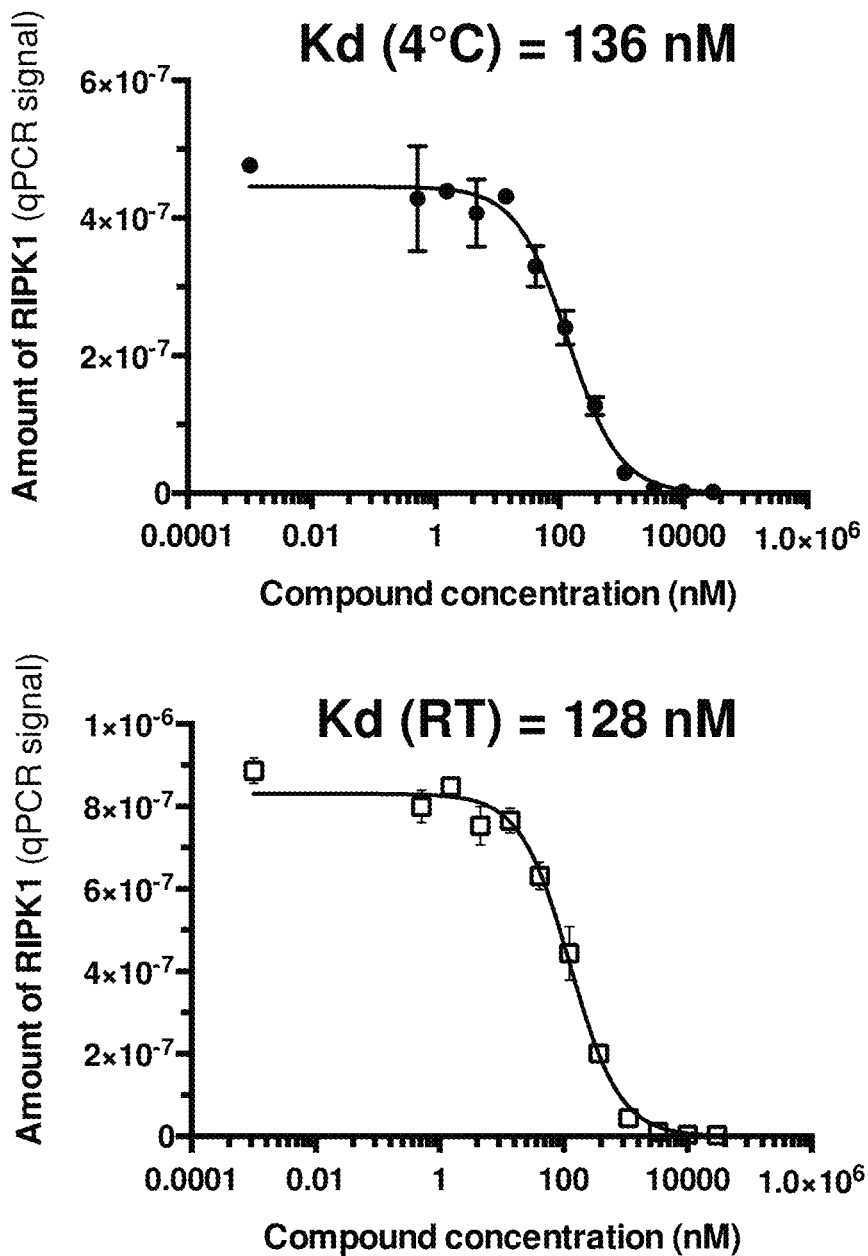
FIG. 9 represents the determination of binding constant (Kd) of compound 1 for its major cellular target RIPK1 at two different temperatures (4° C. and Room Temperature, r.t)

KdELECT is a service of DiscoveRx Corporation, Fremont, USA. This assay is based on a competition binding assay described hereabove. An 11-point 3-fold serial dilution of compound 1 was prepared in 100% DMSO in order to determine the dissociation constant (Kd) at two different temperatures, r.t and 4° C. Kd was then calculated with a standard dose-response curve (reported on FIG. 9) using the Hill equation. The calculated Kd of compound 1 for RIPK1 is 128 nM (n=2) at r.t and 136 nM (n=2) at 4° C. It validates compound 1 as a true ligand of RIPK1 kinase. Indeed, since the Kd value is low (nM range), the interaction between RIPK1 and compound 1 is strong. Moreover, the high affinity of compound 1 for RIPK1 is not affected by low temperature, conditions occurring during cold storage of grafts.

Example 6: In Vitro "Hypoxic Cold Storage" Viability Assays

Figure 10:
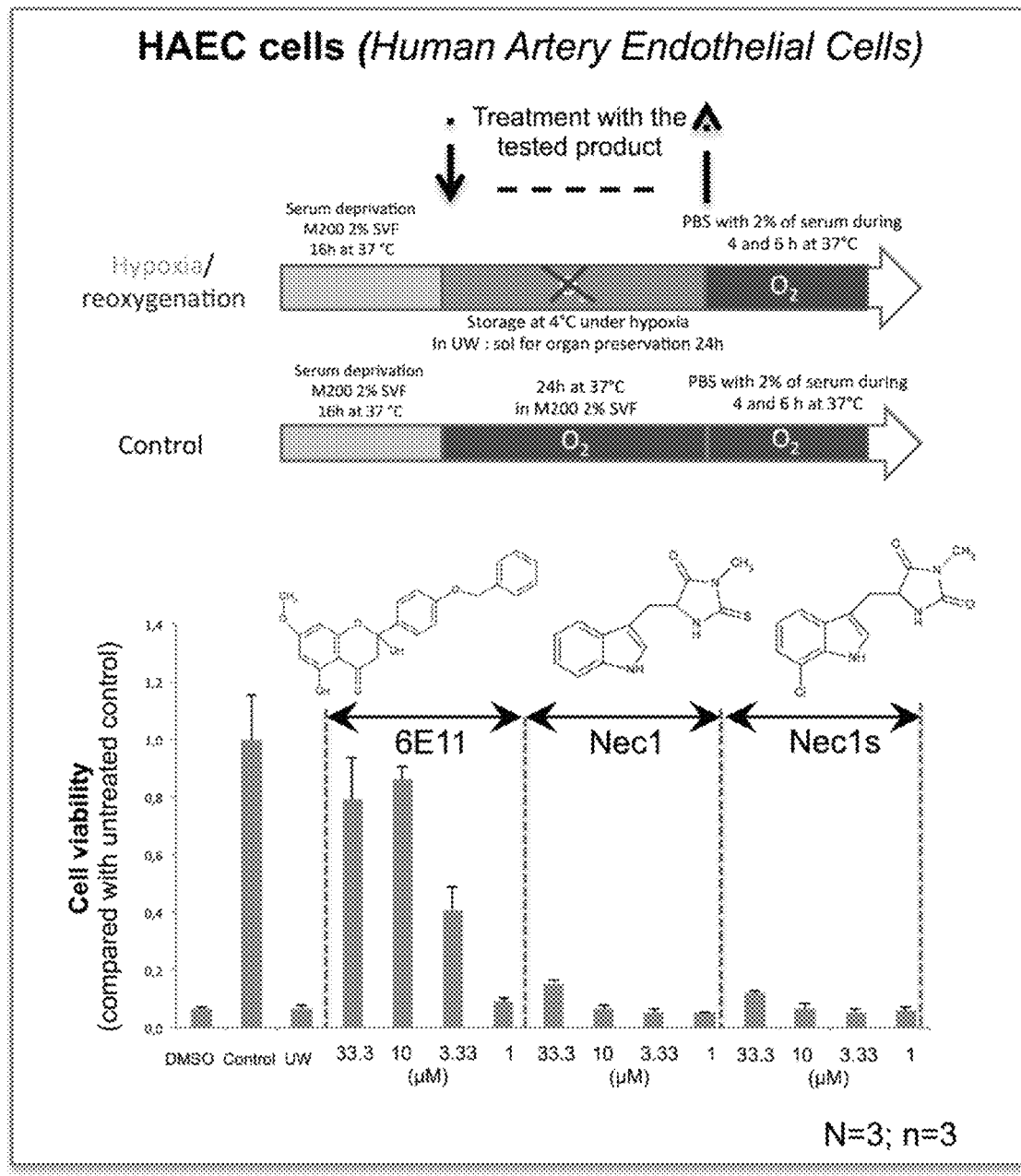
FIG. 10 represents the protection from hypoxic injury of human artery endothelial cells (HAEC) by compound 1 during hypoxic cold storage.
Figure 11:
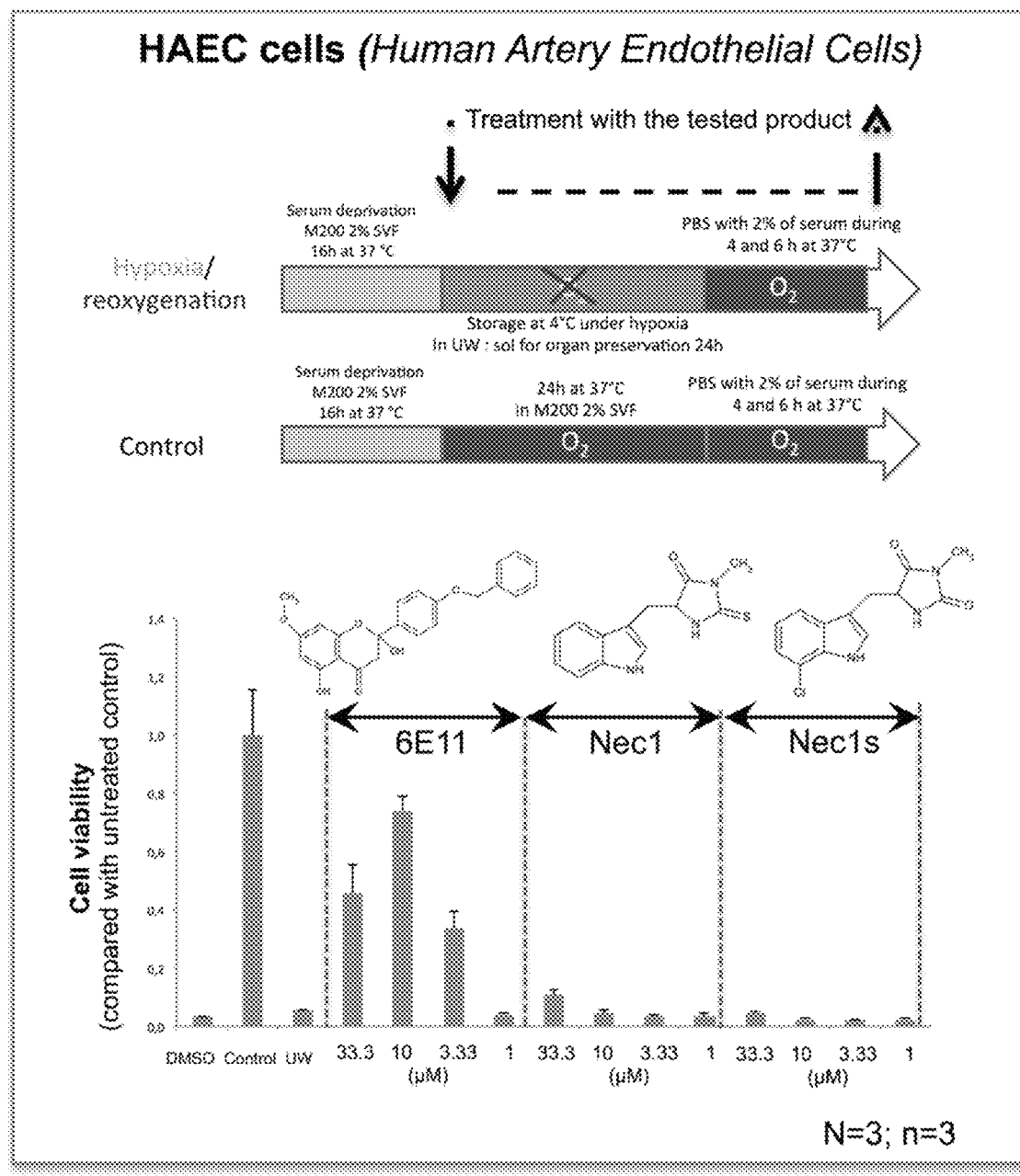
FIG. 11 represents the protection of human artery endothelial cells by compound 1 during both hypoxic cold storage and reoxygenation step.

Human endothelial cells (HAEC) were grown to confluence, then synchronized using depleted media for 16h. For hypothermia/hypoxia, cells were washed twice with PBS then incubated in University of Wisconsin (UW) solution in 95% N$_2$/5% CO$_2$ atmosphere at 4° C. for 24 hours. Compound 1, Nec1 or Nec1s were added to the preservation solution at the indicated dilution (04) during hypoxia (FIG. 10) or during both hypoxia and reoxygenation steps (FIG. 11). Shown are mean+/−SD, n=3. UW are cells treated only with UW preservation solution. Controls are cells not subjected to this protocol (cells are continuously oxygenated) but cultivated for the same amount of time in regular culture conditions. The treatment with compound 1 during hypoxia or during hypoxia and reoxygenation brings measurable benefits on cell survival. Compared to the control inhibitors of necroptosis (Nec-1 and Nec-1s), the effect of compound 1 is significantly better. It should be noted that the hypoxic cold storage mimics the process occurring during graft preservation.

Example 7: In Silicon Analysis of the Theoretical RIPK1-6E11 Complex

Figure 12:
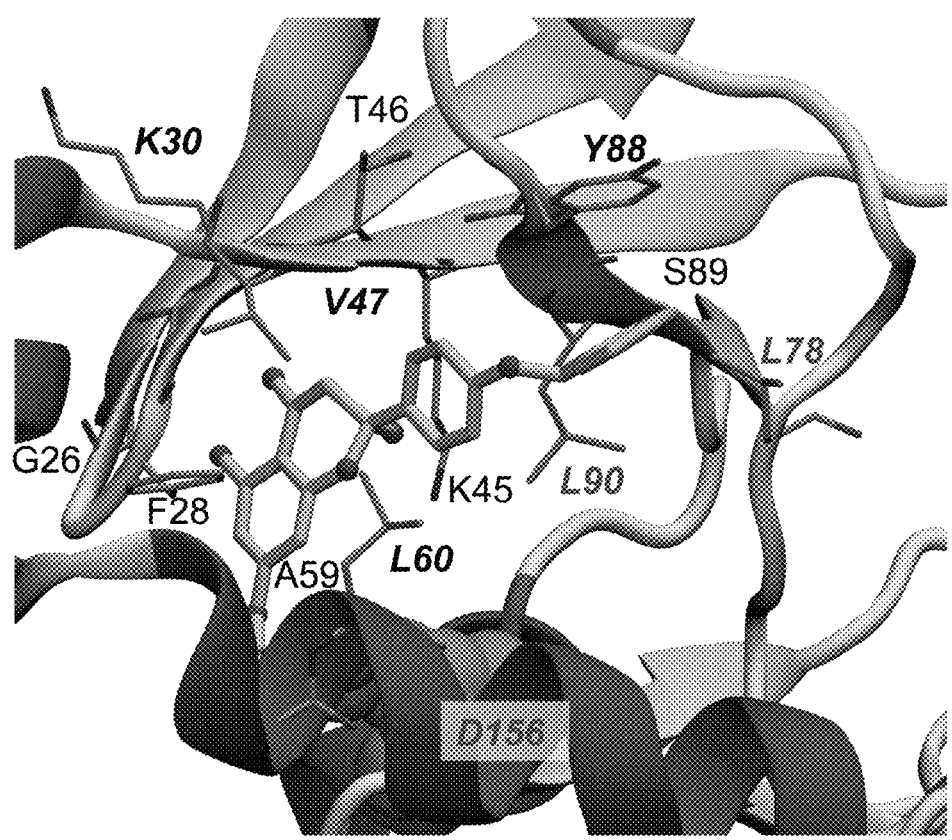
FIG. 12 represents the predictive orientation for compound 1 within the theoretical RIPK1-6E11 complex.
Figure 13A:
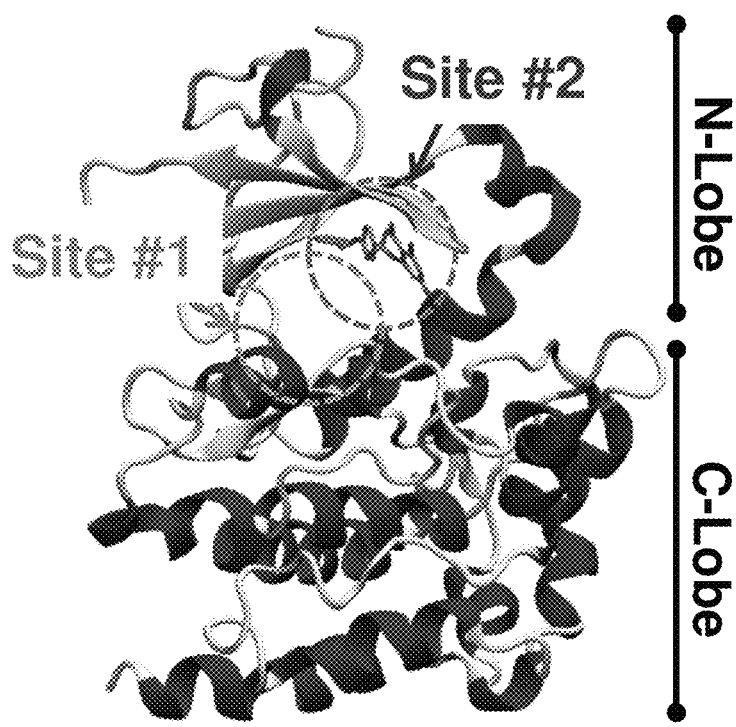
FIGS. 13a et 13b represent the binding sites of compound 1 and Nec1s on RIPK1.
Figure 13B:
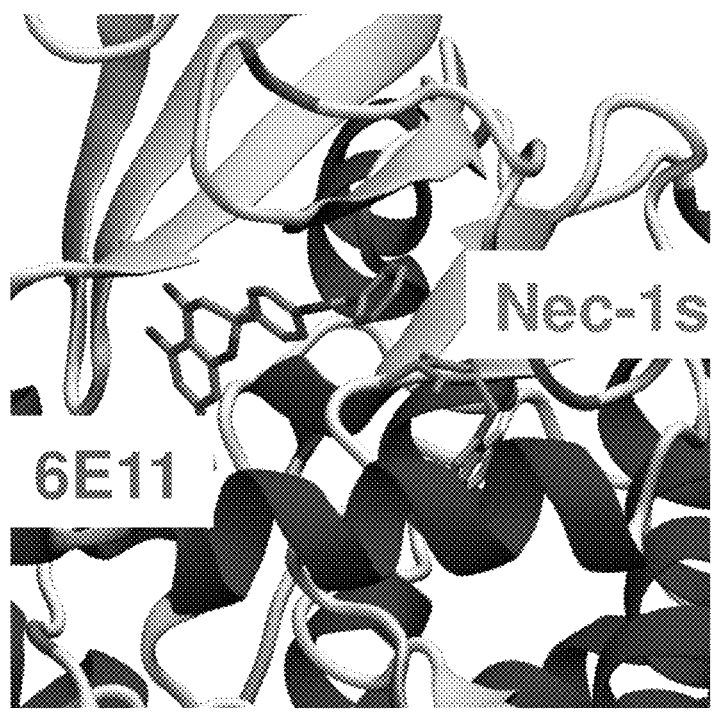

The predictive orientation for compound 1 was studied by in silico analysis of the theoretical RIPK1-6E11 complex. Stable contact residues defining a pharmacophore and determined on the most representative structural model included six key amino acids Lys30, Val47, Leu60, Leu78, Tyr88 and Leu90 (FIG. 12). Surrounding residues (4.0 Å cut-off distance) describing the compound 1 binding pocket observed over the molecular docking simulation trajectory also comprised of Phe28, Val31, Lys45, Thr46, Ala59, Glu63, Val81, Ile83, Ser89 and Asp156. We should note that among these amino acids, three of them (Leu78, Leu90 and Asp156) have been already described to be involved in the interaction with necrostatins (Xie et al. Structure 2013, 21, 493-499). Molecular dynamic (MD) simulation of RIPK1-6E11 model allowed us to improve the preferential binding mode identified by docking calculations which is different from Nec-1s (FIGS. 13a,b). The binding site of Nec-1s is marked as "site #1" on FIG. 13a. From analysis of the most frequent contacts of the compound to the kinase, we are able to propose that compound 1 should bind RIPK1 kinase through tight hydrophobic interactions and a non-specific hydrogen bond (HB), as well as other transient HB interactions observed during the simulation (FIGS. 13a,b). The putative binding site #2 of compound 1 is marked as "site #2" on FIG. 13b. Our simulations suggest that compound 1 fits tightly in an alternative and putative cleft surrounded notably by the RIPK1 catalytic triad residues: Lys45, Glu63 and Asp156. This cleft of RIPK1 is mainly hydrophobic but richer in hydrogen bond acceptors than the kinase hinge within the ATP-binding site. Interestingly, this model shows that compound 1 does not make any interaction with the kinase hinge in this conformation of RIPK1 regardless of hydrogen bonds. Moreover, this proposed binding mode for compound 1 occupying a lipophilic pocket in a cleft near the substrate binding site of RIPK1 indicates that this compound is likely a type III kinase inhibitor. This binding mode is in line with the high selectivity of compound 1 detected by the KINOMEscan$^{SM}$ Assay (FIG. 8) and also with the non-ATP competitive mode of inhibition (reported on FIG. 7).

Example 8: Effect of Compound 1 on Both Ferroptosis and Oxytosis Programmed Cell-Death Routes Murine hippocampal neuronal cell line HT22 was treated with 10 mM of (L)-glutamate (oxytosis initiator) or 1 μM erastin (ferroptosis initiator).

Figure 14:
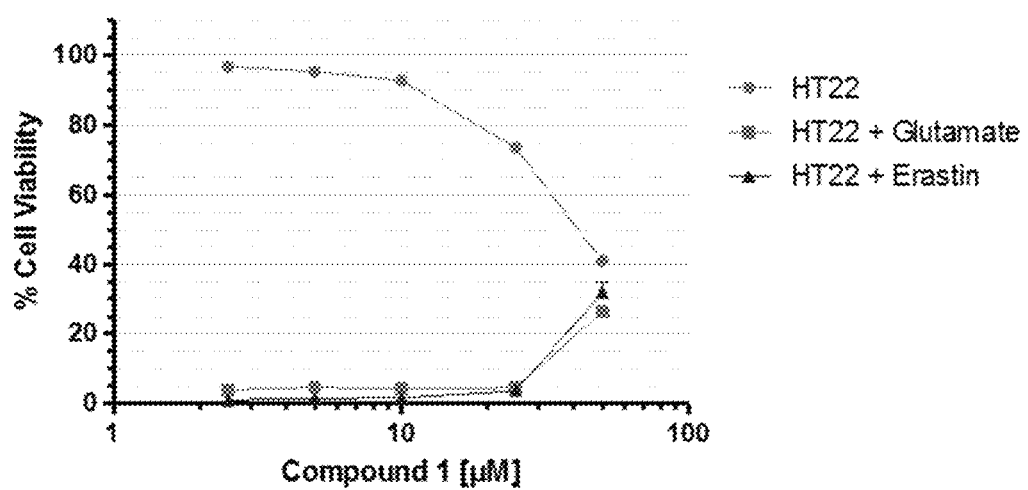
FIG. 14 represents the dose-dependent protection from ferroptosis (induced by erastin) and Glutamate-induced oxidative toxicity of murine hippocampal neuronal cell line HT22 by compound 1.

In this assay, 5,000 cells were seeded per well and treated with increasing concentrations of compound 1 (2.50-5.00-10.00-25.00-50.00 μM) with or without 1 μM erastin or 10 mM L-glutamate. Cells were then incubated at 37° C., 5% $CO_2$ for 24 hours before performing MTS viability assay. Cell viability was monitored using CellTiter 96® AQueous Non-Radioactive Cell Proliferation Assay (Promega, Fitchburg, WI, USA), based on the water-soluble tetrazolium compound MTS (3-[4,5-dimethylthiazol-2-yl]-5-[3-carboxymethoxy-phenyl]-2-[4-sulfophenyl]-2H-tetrazolium, inner salt) according to the manufacturers instructions. As it appears from FIG. 14, >25 μM of compound 1 protects cells from death induced by both L-glutamate and erastin.

Example 9: Effect of Compound 1 on a Cellular Model of Age-Related Macular Degeneration (AMD)

Figure 15A:
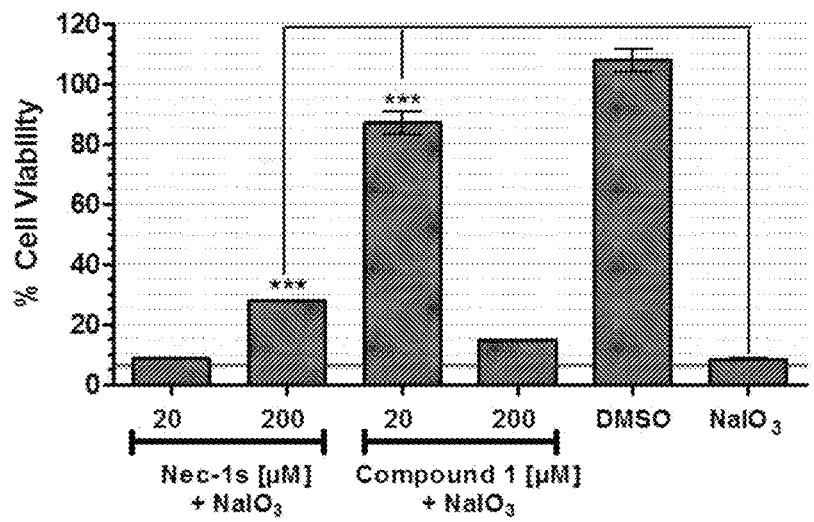
FIGS. 15a and 15b represent the dose-dependent protection of compound 1 from the NaIO$_3$-induced retinal cell death (ARPE-19, a human retinal pigment epithelial cell line).
Figure 15B:
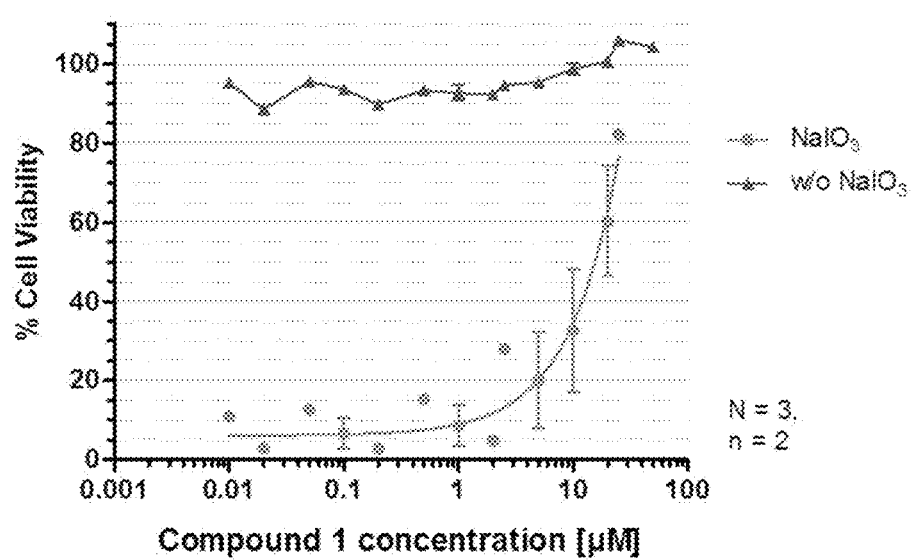

At it was previously shown (Hanus et al. Cell Death Discov. 2016, 2, 16054), $NaIO_3$ is an oxidizing agent that induces necroptosis in retinal pigment epithelial cell line that can be inhibited by 200 μM of necrostatin-1. The experiment described in the cited literature was reproduced to detect the effect of compound 1. Human retinal pigment epithelial cell line, ARPE-19, was treated with 10 mM of $NaIO_3$ as cellular model of age-related macular degeneration (AMD). In this assay, 10,000 cells were seeded per well and treated with 20 or 200 μM of compound 1 or Nec-1s (a specific RIPK-1-dependent necroptosis inhibitor) (FIG. 15a) or increasing concentrations of compound 1 (0.01, 0.02, 0.05, 0.10, 0.20, 0.50, 1.00, 2.00, 2.50, 5.00, 10.00, 20.00, 25.00 μM) (FIG. 15b) with or without 10 mM of $NaIO_3$. Cells were then incubated at 37° C., 5% $CO_2$ for 24 hours before performing MTS viability assay. Cell viability was monitored using CellTiter 96® AQueous Non-Radioactive Cell Proliferation Assay (Promega, Fitchburg, WI, USA), based on the water-soluble tetrazolium compound MTS (3-[4,5-dimethylthiazol-2-yl]-5-[3-carboxymethoxy-phenyl]-2-[4-sulfophenyl]-2H-tetrazolium, inner salt) according to the manufacturers instructions. As it appears from FIGS. 15a and 15b, subtoxic concentration of compound 1 (+/−20 μM) protects significantly cells from death induced by $NaIO_3$ (N=3, n=2, mean±SD, *** P<0.001).

Example 10: Effect of Compound 1 on Cold-Induced Cell Death (Cold-Stress Preservation)

Figure 16A:
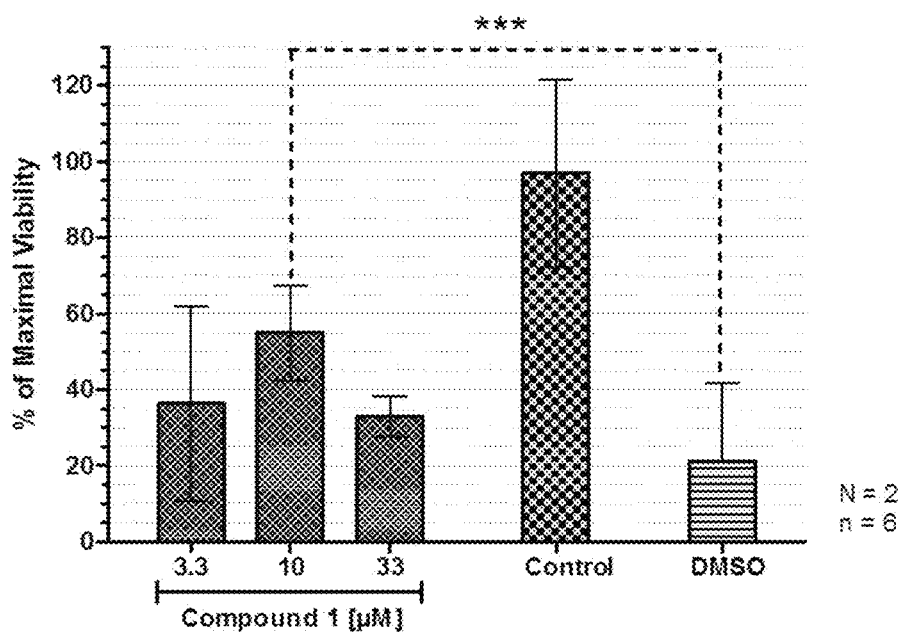
FIGS. 16a and 16b represent the dose-dependent protection of compound 1 from the cold-induced cell death (LLC-PK1 cells, porcine kidney proximal tubule cell line).
Figure 16B:
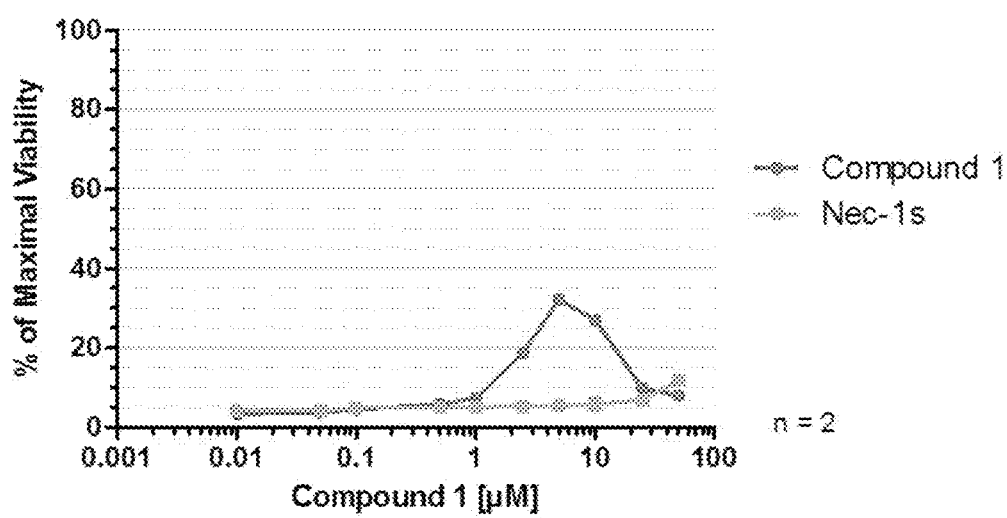

At it was previously shown (Ahlenstiel et al. Transplantation 2016, 81(2), 231-239), cold storage induces a cell-death process. Porcine LLC-PK1 cells (kidney proximal tubule cell line) were stored at approximately 4° C. during 24 hours with or without the tested molecules. In this assay, 5,000 cells were seeded per well and treated with increasing concentrations of compound 1 or Nec-1s (0.01, 0.05, 0.10, 0.50, 1.00, 2.50, 5.00, 10.00, 25.00 and 50.00 μM) and stored for 24 hours at 4° C. Cells were then incubated at 37° C., 5% $CO_2$ before performing MTS viability assay. Cell viability was monitored using CellTiter 96® AQueous Non-Radioactive Cell Proliferation Assay (Promega, Fitchburg, WI, USA), based on the water-soluble tetrazolium compound MTS (3-[4,5-dimethylthiazol-2-yl]-5-[3-carboxymethoxy-phenyl]-2-[4-sulfophenyl]-2H-tetrazolium, inner salt) according to the manufacturers instructions. As it appears from FIGS. 16a and 16b, compound 1 protects cells from death induced by cold storage with a maximal activity at 504. Nec-1s is inactive at the tested doses (FIG. 16a, N=2, n=6, mean±SD, *** P<0.05; FIG. 16b, n=2).

Example 11: Effect of Compound 1 on $H_2O_2$-Induced Necrosis (Anti-Oxidant Property)

Figure 17:
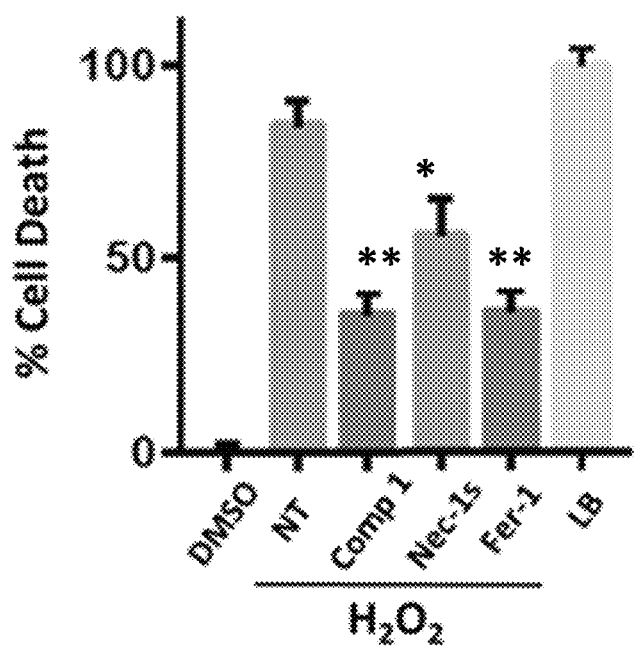
FIG. 17 represents the protection of rat embryonic myoblastic H9C2 cells by compound 1 from necrosis induced by H$_2$O$_2$.

The rat embryonic myoblastic H9C2 cells were cultured at 10,000 cells/well in 96-well-plates for 24 hours at 37° C./5% $CO_2$. Then, cells were treated or not (DMSO) with 800 μM $H_2O_2$ for 24 hours after a 2 hours pretreatment or not (NT) with 10 μM compound 1 (comp 1), 10 μM Necrostatin-1s (Nec-1s), or 10 µM Ferrostatin-1 (Fer-1). LB corresponds to cells treated with a lysis buffer (100% of cell death). Cell cytotoxicity was determined by a colorimetric assay quantitatively measuring lactate dehydrogenase (LDH) released into the cytosol. As it appears from FIG. 17, compound 1 protects from death induced by $H_2O_2$ in the same extent as Fer-1, Nec-1s being less effective (FIG. 17, N=2, n=6, mean±SD, ** P<0.005; * P<0.05).

The invention claimed is:

1. A pharmaceutical composition comprising at least one compound of the following general formula (I):

(I)

[Chemical structure]

or a pharmaceutically acceptable salt and/or solvate thereof, wherein:
$X_1$ represents a $(C_1-C_6)$alkyl an aryl, an aryl-$(C_1-C_6)$ alkyl group or an $OR_X$ group, wherein
$R_X$ is selected from a $(C_1-C_6)$alkyl, an aryl and an aryl-$(C_1-C_6)$alkyl group,
$X_2$ and $X_3$ each represent, independently of each other, a hydrogen atom or a $(C_1-C_6)$alkyl group,
$Y_1$, $Y_2$ and $Y_3$ each represent, independently of each other, a hydrogen atom, a $(C_1-C_6)$alkyl, an aryl, an aryl-$(C_1-C_6)$alkyl group, an OH or an $OR_Y$ group,
with at least one of $Y_1$, $Y_2$ and $Y_3$ representing a $(C_1-C_6)$alkyl, an aryl, an aryl-$(C_1-C_6)$alkyl group or an $OR_Y$ group, wherein
$R_Y$ is selected from a $(C_1-C_6)$alkyl, an aryl and an aryl-$(C_1-C_6)$alkyl group,
and at least one pharmaceutically acceptable excipient.

2. The pharmaceutical composition according to claim 1, wherein the compound is of the following general formula (II):

(II)

[Chemical structure]

or a pharmaceutically acceptable salt and/or solvate thereof, wherein $R_X$ represents a $(C_1-C_6)$alkyl group and $R_Y$ represents an aryl-$(C_1-C_6)$alkyl group.

3. The pharmaceutical composition according to claim 1, wherein the pharmaceutically acceptable excipient is selected from the group consisting of long-term stabilizers, drug absorption enhancers, viscosity reducers and solubility enhancers.

4. The pharmaceutical composition according to claim 3, wherein the pharmaceutically acceptable excipient is a solubility enhancer.

5. The pharmaceutical composition according to claim 1, wherein it further comprises at least one other active ingredient.

6. The pharmaceutical composition according to claim 5, wherein the other active ingredient is selected from the group consisting of another cellular necroptosis inhibitor, an apoptosis inhibitor, an autophagy inhibitor, a ferroptosis inhibitor, an inhibitor of mitochondrial permeability transition (MPT) pore-dependent necrosis, a cyclophilin inhibitor, a Cyclin-dependent kinase 5 (CDK5) inhibitor, a parthanatos inhibitor, a thrombin inhibitor, an antioxidant an inflammatory inhibitor and combinations thereof.

7. The pharmaceutical composition according to claim 6, wherein the other active ingredient is an antioxidant.

8. A combination product comprising:
(i) at least one compound of the following general formula (I):
or a pharmaceutically acceptable salt and/or solvate thereof, wherein:
$X_1$ represents a $(C_1-C_6)$alkyl an aryl, an aryl-$(C_1-C_6)$ alkyl group or an $OR_X$ group, wherein $R_X$ is selected from a $(C_1-C_6)$alkyl, an aryl and an aryl-$(C_1-C_6)$ alkyl group,
$X_2$ and $X_3$ each represent, independently of each other, a hydrogen atom or a $(C_1-C_6)$alkyl group,
$Y_1$, $Y_2$ and $Y_3$ each represent, independently of each other, a hydrogen atom, a $(C_1-C_6)$alkyl, an aryl, an aryl-$(C_1-C_6)$alkyl group, an OH or an $OR_Y$ group,
with at least one of $Y_1$, $Y_2$ and $Y_3$ representing a $(C_1-C_6)$alkyl, an aryl, an aryl-$(C_1-C_6)$alkyl group or an $OR_Y$ group, wherein
$R_Y$ is selected from a $(C_1-C_6)$alkyl, an aryl and an aryl-$(C_1-C_6)$alkyl group, and
(ii) at least another active ingredient selected from the group consisting of another cellular necroptosis inhibitor, an apoptosis inhibitor, an autophagy inhibitor, a ferroptosis inhibitor, an inhibitor of mitochondrial permeability transition (MPT) pore-dependent necrosis, a cyclophilin inhibitor, a Cyclin-dependent kinase 5 (CDK5) inhibitor, a parthanatos inhibitor, a thrombin inhibitor, an antioxidant an inflammatory inhibitor and combinations thereof,
separate from the at least one compound of formula (I), for simultaneous, separate or sequential administration.

9. The combination product according to claim 8, wherein the compound is of the following general formula (II):
or a pharmaceutically acceptable salt and/or solvate thereof, wherein $R_X$ represents a $(C_1-C_6)$alkyl group and $R_Y$ represents an aryl-$(C_1-C_6)$alkyl group.

10. The combination product according to claim 8, wherein the other active ingredient is an antioxidant.

11. The pharmaceutical composition according to claim 3, wherein the pharmaceutically acceptable excipient is a drug absorption enhancer.

* * * * *